(12) United States Patent
Iguchi et al.

(10) Patent No.: US 10,739,548 B2
(45) Date of Patent: Aug. 11, 2020

(54) OPTICAL UNIT AND ENDOSCOPE

(71) Applicant: OLYMPUS CORPORATION, Tokyo (JP)

(72) Inventors: Takehiko Iguchi, Hino (JP); Takeshi Saito, Tokorozawa (JP); Sho Nakamura, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 363 days.

(21) Appl. No.: 15/730,827

(22) Filed: Oct. 12, 2017

(65) Prior Publication Data
US 2018/0031800 A1    Feb. 1, 2018

Related U.S. Application Data

(63) Continuation of application No. PCT/JP2015/061626, filed on Apr. 15, 2015.

(51) Int. Cl.
*G02B 7/04* (2006.01)
*A61B 1/00* (2006.01)
(Continued)

(52) U.S. Cl.
CPC ............ *G02B 7/04* (2013.01); *A61B 1/00096* (2013.01); *A61B 1/00158* (2013.01);
(Continued)

(58) Field of Classification Search
CPC ............ A61B 1/00096; A61B 1/00158; A61B 1/00188; G02B 23/2438; G02B 23/2476; G02B 7/09; G02B 15/14
See application file for complete search history.

(56) References Cited

U.S. PATENT DOCUMENTS 5,541,777 A *  7/1996  Sakamoto ............... G02B 7/102
                                                    310/13
6,099,467 A *  8/2000  Kehr .................. A61B 1/00188
                                                    359/822
(Continued)

FOREIGN PATENT DOCUMENTS

JP      2006-276565 A      10/2006
JP      2010-243195 A      10/2010
(Continued)

OTHER PUBLICATIONS

International Search Report dated Jul. 14, 2015 received in PCT/JP2015/061626.

*Primary Examiner* — Timothy J Neal
*Assistant Examiner* — Jae Woo
(74) *Attorney, Agent, or Firm* — Scully, Scott, Murphy & Presser, P.C.

(57) ABSTRACT

An optical unit includes: a cylindrical fixing member configured to retain at least one of an object-side fixed lens group and an image-side fixed lens group; a cylindrical movable member configured to retain a movable lens group between the groups and arranged on a radial-direction inner side of the fixing member slidablly with respect to the fixing member, the cylindrical movable member having a same central axis as the cylindrical fixing member; a voice coil motor including: a coil arranged in the fixing member; and magnets arranged on the movable member and magnetically polarized in a direction intersecting with the central axis, the voice coil motor being capable of moving the movable member relative to the fixing member along a direction of the central axis; and a rotation restricting member configured to restrict rotation of the movable member about the central axis with respect to the fixing member.

5 Claims, 18 Drawing Sheets

(51) Int. Cl.
*A61B 1/05* (2006.01)
*G02B 23/24* (2006.01)
*G02B 7/08* (2006.01)
*A61B 1/045* (2006.01)

(52) U.S. Cl.
CPC ............ *A61B 1/00188* (2013.01); *A61B 1/05* (2013.01); *G02B 7/08* (2013.01); *G02B 23/2438* (2013.01); *G02B 23/2476* (2013.01); *A61B 1/045* (2013.01)

(56) References Cited

U.S. PATENT DOCUMENTS

| | | | | |
|---|---|---|---|---|
| 9,448,397 | B2* | 9/2016 | Makiyama | A61B 1/00096 |
| 9,924,854 | B2* | 3/2018 | Iwasaki | A61B 1/00 |
| 10,120,181 | B2* | 11/2018 | Kono | A61B 1/00096 |
| 10,244,932 | B2* | 4/2019 | Fujii | G02B 23/2438 |
| 10,278,565 | B2* | 5/2019 | Wieters | A61B 1/00071 |
| 10,459,192 | B2* | 10/2019 | Kono | G02B 23/2438 |
| 2008/0272869 | A1* | 11/2008 | Takayama | A61B 1/00188 335/219 |
| 2009/0015948 | A1* | 1/2009 | Wada | G02B 7/08 359/824 |
| 2009/0073585 | A1* | 3/2009 | Yamashita | G02B 7/022 359/824 |
| 2010/0328791 | A1* | 12/2010 | Jung | G03B 17/02 359/824 |
| 2011/0210689 | A1* | 9/2011 | Vogel | A61B 1/0016 318/631 |
| 2011/0267712 | A1* | 11/2011 | Umeda | G03B 5/02 359/823 |
| 2012/0063005 | A1* | 3/2012 | Aoshima | G03B 9/06 359/699 |
| 2013/0314517 | A1* | 11/2013 | Makiyama | A61B 1/045 348/65 |
| 2015/0287508 | A1* | 10/2015 | Wieters | A61B 17/00 335/253 |
| 2016/0018625 | A1* | 1/2016 | Morishima | G02B 7/04 359/824 |
| 2016/0041381 | A1* | 2/2016 | Makiyama | A61B 1/00096 359/824 |
| 2016/0282601 | A1* | 9/2016 | Kono | A61B 1/05 |
| 2016/0374543 | A1* | 12/2016 | Wieters | A61B 1/00071 600/167 |

FOREIGN PATENT DOCUMENTS

| | | |
|---|---|---|
| JP | 2011-221212 A | 11/2011 |
| JP | 2013-003434 A | 1/2013 |
| JP | 2015-114651 A | 6/2015 |
| JP | 2015-148704 A | 8/2015 |
| WO | 2013/054787 A1 | 4/2013 |

* cited by examiner

OPTICAL UNIT AND ENDOSCOPE

CROSS-REFERENCE TO RELATED APPLICATIONS

This application is a continuation of PCT international application Ser. No. PCT/JP2015/061626 filed on Apr. 15, 2015 which designates the United States, incorporated herein by reference.

BACKGROUND

The present disclosure relates to an optical unit and an endoscope.

In the related art, there is disclosed an endoscope having a movable lens frame to which a lens is attached and having a zoom function for changing photographing magnification by moving the movable lens frame forward and backward (refer to, for example, JP 2010-243195 A).

SUMMARY

An optical unit according to one aspect of the present disclosure includes: a cylindrical fixing member configured to retain at least one of an object-side fixed lens group and an image-side fixed lens group; a cylindrical movable member configured to retain a movable lens group between the object-side fixed lens group and the image-side fixed lens group and arranged on a radial-direction inner side of the fixing member so as to be slidable with respect to the fixing member, the cylindrical movable member having a same central axis as the cylindrical fixing member; a voice coil motor including: a coil arranged in the fixing member; and magnets arranged on the movable member and magnetically polarized in a direction intersecting with the central axis, the voice coil motor being capable of moving the movable member relative to the fixing member along a direction of the central axis; and a rotation restricting member configured to restrict rotation of the movable member about the central axis with respect to the fixing member.

An endoscope according to another aspect of the present disclosure is an endoscope which is inserted into an inside of a subject and observes the inside of the subject, and includes: an optical unit including: a cylindrical fixing member configured to retain at least one of an object-side fixed lens group and an image-side fixed lens group; a cylindrical movable member configured to retain a movable lens group between the object-side fixed lens group and the image-side fixed lens group and arranged on a radial-direction inner side of the fixing member so as to be slidable with respect to the fixing member, the cylindrical movable member having a same central axis as the cylindrical fixing member; a voice coil motor including: a coil arranged in the fixing member; and magnets arranged on the movable member and magnetically polarized in a direction intersecting with the central axis, the voice coil motor being capable of moving the movable member relative to the fixing member along a direction of the central axis; and a rotation restricting member configured to restrict rotation of the movable member about the central axis with respect to the fixing member; and an image sensor configured to convert light condensed by the optical unit into an electrical signal.

The above and other objects, features, advantages and technical and industrial significance of this disclosure will be better understood by reading the following detailed description of presently preferred embodiments of the disclosure, when considered in connection with the accompanying drawings.

DETAILED DESCRIPTION

Hereinafter, modes for carrying out the disclosure (hereinafter referred to as "embodiments") will be described.

First Embodiment

Figure 1:
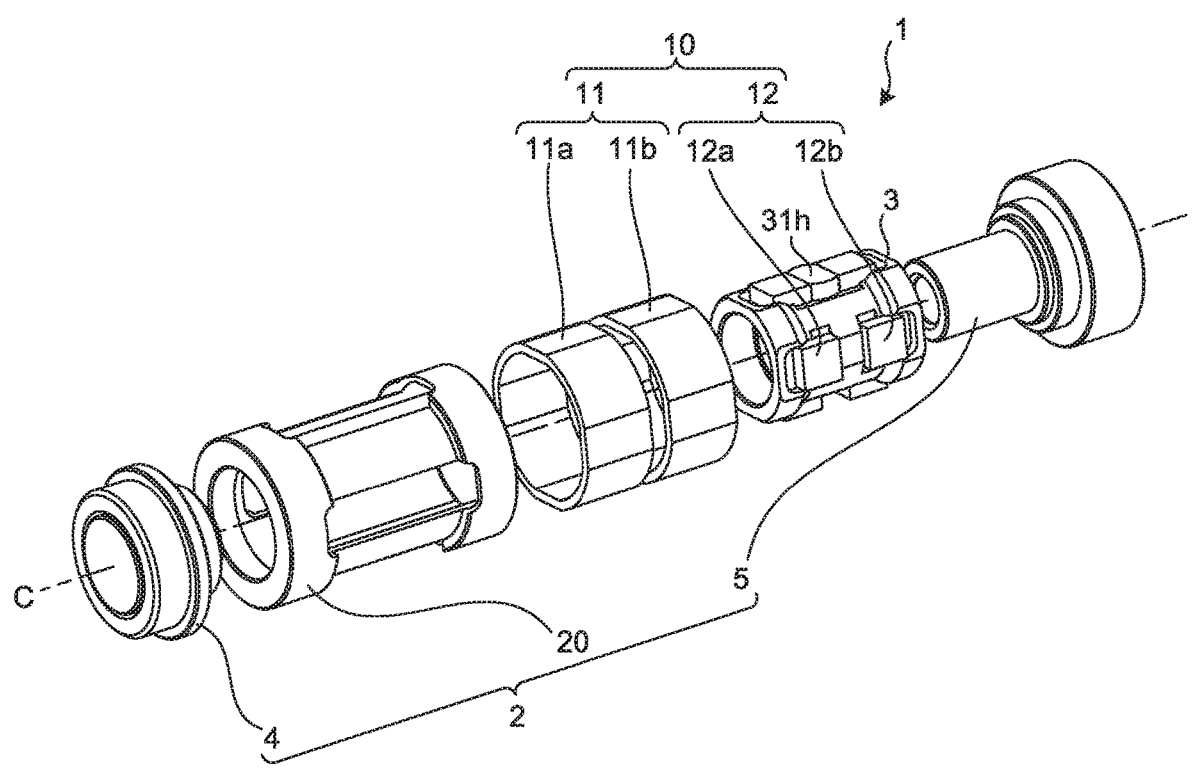
FIG. 1 is an exploded perspective view illustrating a configuration of an optical unit according to a first embodiment of the disclosure.
Figure 2:
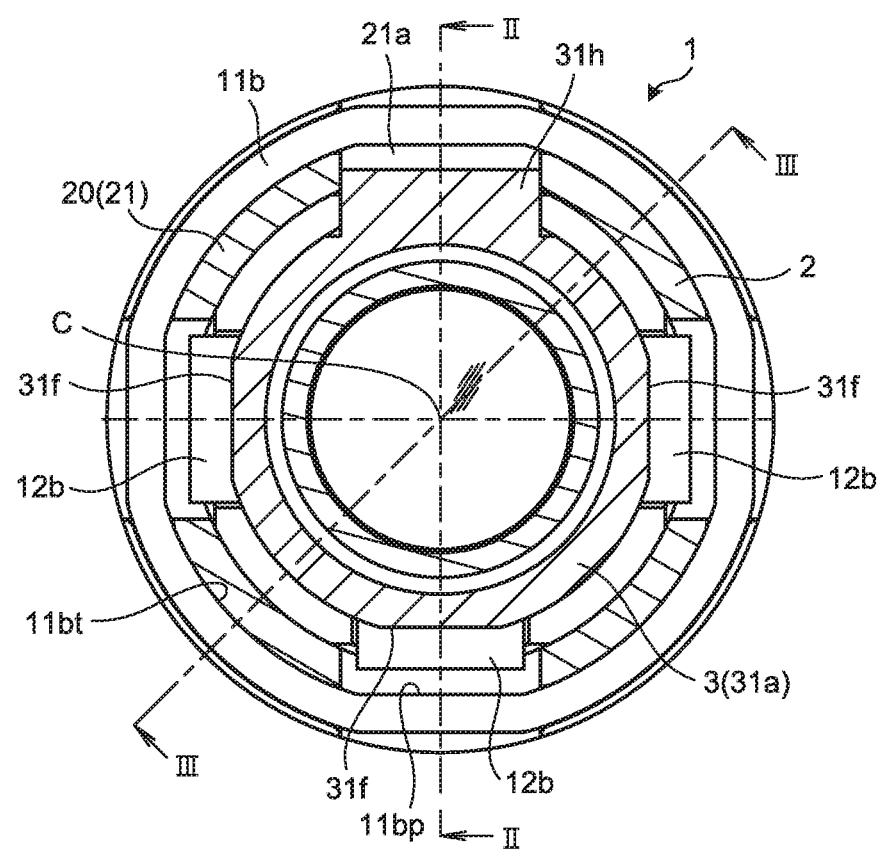
FIG. 2 is a cross-sectional view illustrating a configuration of main components of the optical unit according to the first embodiment of the disclosure.
Figure 3:
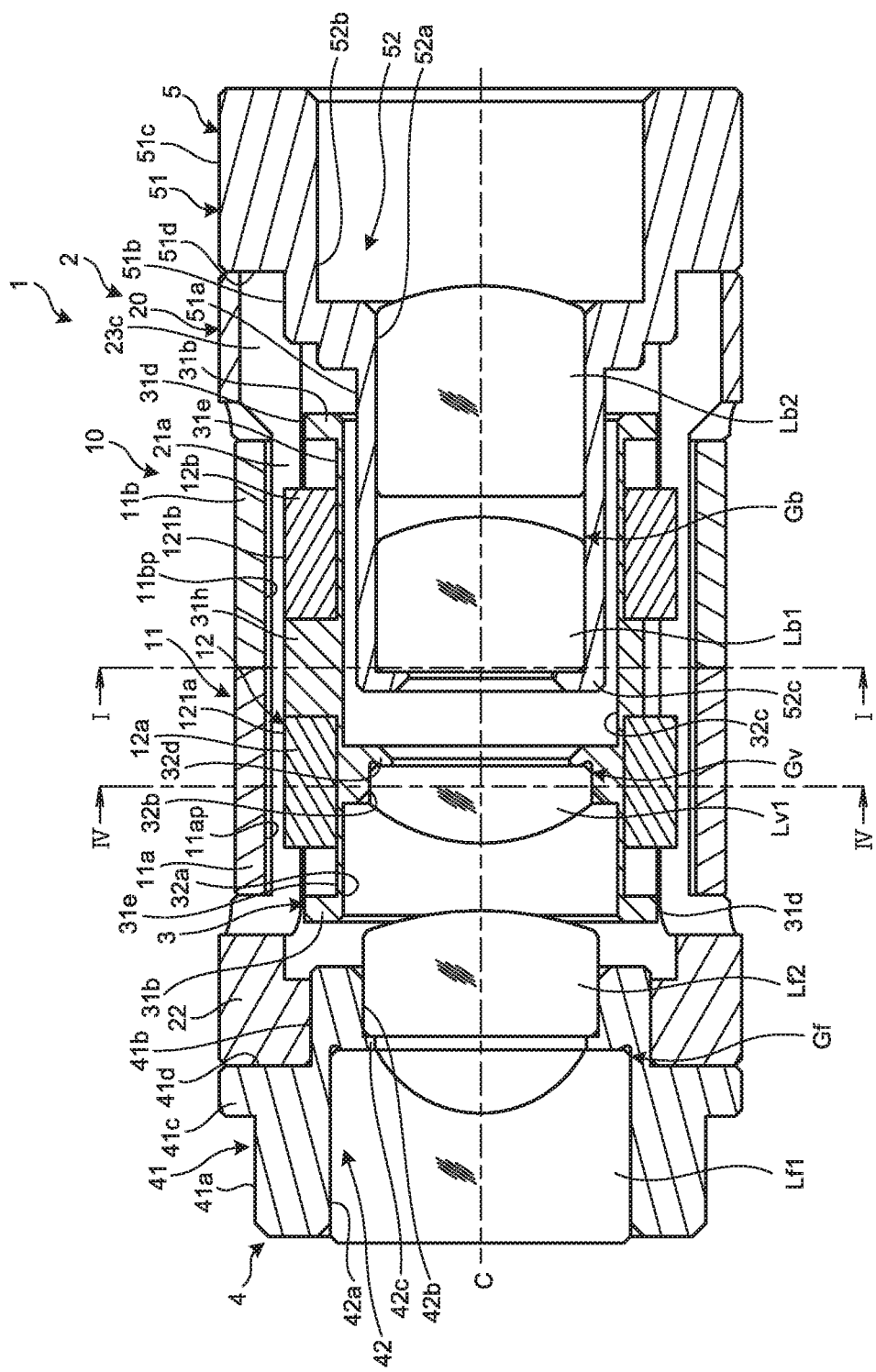
FIG. 3 is a cross-sectional view of the optical unit as viewed in a cross section taken along line II-II of FIG. 2.
Figure 4:
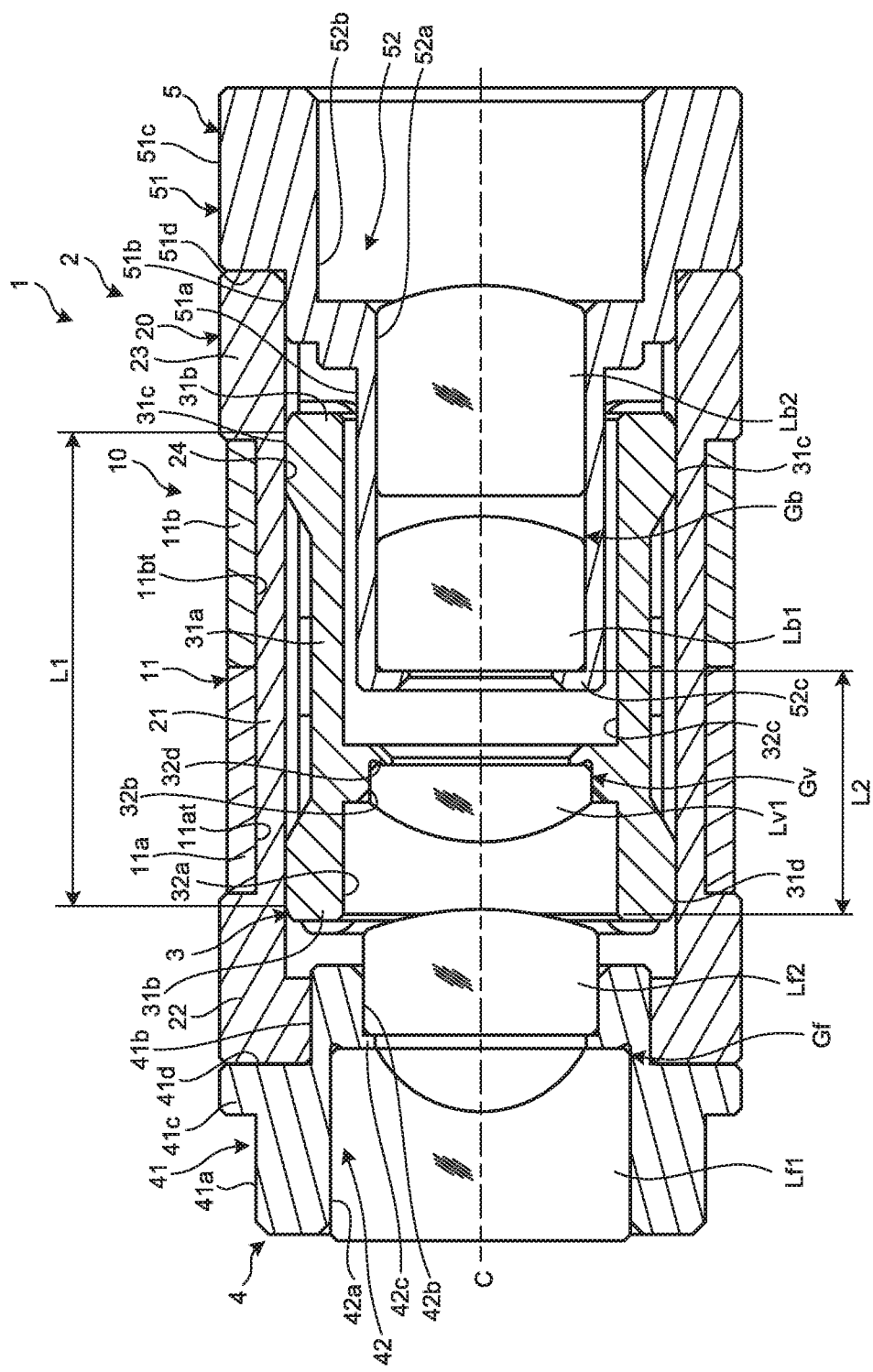
FIG. 4 is a cross-sectional view of the optical unit as viewed in a cross section taken along line III-III of FIG. 2.

FIG. 1 is an exploded perspective view illustrating a configuration of an optical unit according to a first embodiment of the disclosure. FIG. 2 is a cross-sectional view illustrating a configuration of main components of the optical unit according to the first embodiment. FIG. 3 is a cross-sectional view of the optical unit as viewed in a cross section taken along line II-II of FIG. 2. FIG. 4 is a cross-sectional view of the optical unit as viewed in a cross section taken along line III-III of FIG. 2. In addition, FIG. 2 is also a cross-sectional view of the optical unit as viewed in a cross section taken along line I-I of FIG. 3.

An optical unit 1 illustrated in FIGS. 1 to 4 is configured to include a fixing member 2, a movable member 3 which is movable with respect to the fixing member 2, a voice coil motor 10 which generates a driving force for moving the movable member 3 with respect to the fixing member 2.

The fixing member 2 is configured to include a fixing member main body 20, a front frame portion 4 which retains an object-side fixed lens group Gf on the object side of a movable lens group Gv retained by the movable member 3 and is attached to the object side of the fixing member main body 20, and a rear frame portion 5 which retains an image-side fixed lens group Gb on the image side of the movable lens group Gv and is attached to the image side of the fixing member main body 20.

Figure 5:
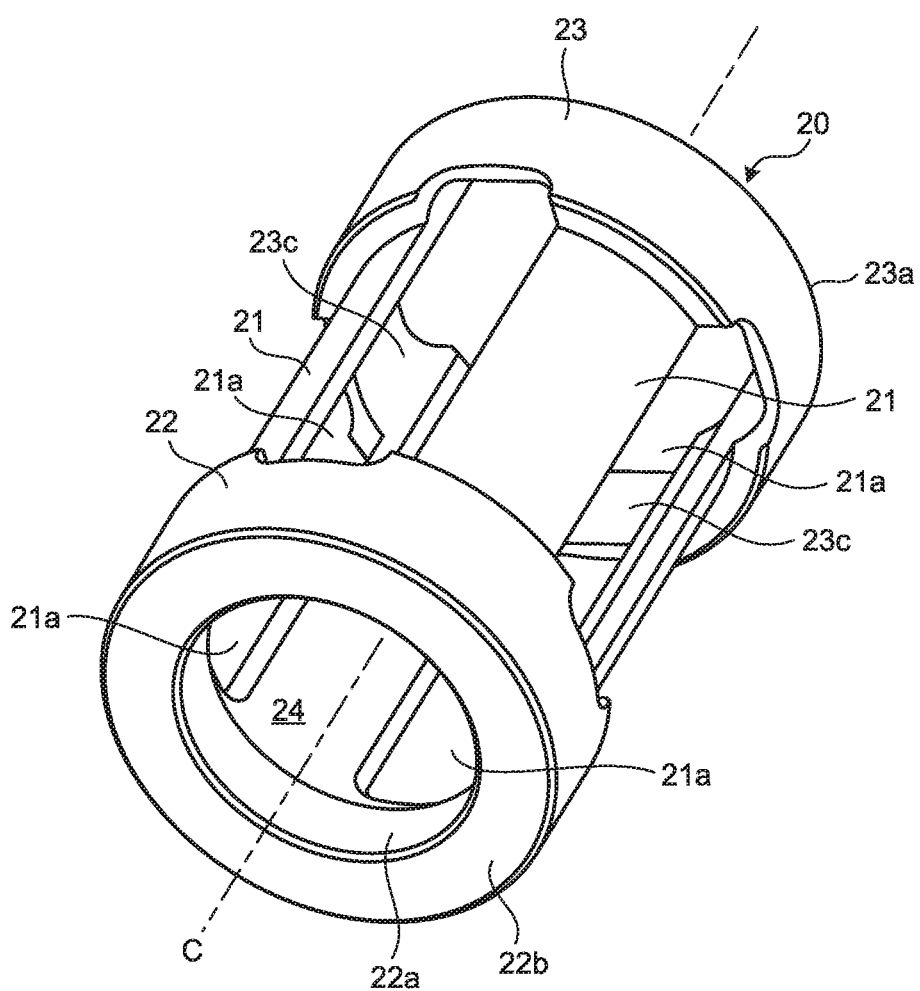
FIG. 5 is a perspective view illustrating a configuration of a fixing member main body of the optical unit according to the first embodiment of the disclosure.

FIG. 5 is a perspective view illustrating the configuration of the fixing member main body 20. The fixing member main body 20 illustrated in the figure is configured with a cylindrical member centered on a predetermined axis C. The fixing member main body 20 is configured to include a cylinder 21 having the axis C as a central axis, an object-side thick portion 22 formed on the object side in the direction of the axis C with respect to the cylinder 21, and an image-side thick portion 23 formed on the side opposite to that of the object-side thick portion 22 in the direction of the axis C with respect to the cylinder 21. The fixing member main body 20 has rotational symmetry of 90° with respect to the axis C. Hereinafter, the side opposite to the object side in the direction of the axis C is referred to as the image side.

In the cylinder 21, a recessed portion 21a is formed. Specifically, four recessed portions 21a penetrating in the radial direction of the cylinder 21 are formed at intervals of 90° along the peripheral direction with respect to the longitudinal central axis C of the cylinder 21. The surface on the radial-direction inner side of the cylinder 21 excluding the recessed portions 21a is a cylindrical surface and is a fixed-side sliding surface 24 for guiding and supporting the movable member 3. The fixed-side sliding surface 24 has a shape divided in the peripheral direction by the recessed portions 21a.

The object-side thick portion 22 is formed so as to protrude radially outward and radially inward from the cylinder 21. The image-side thick portion 23 is formed so as to protrude radially outward from the cylinder 21. On the fixed-side sliding surface 24 on the radial-direction inner side of the image-side thick portion 23, grooves 23c are formed. When the movable member 3 is assembled, magnets 12 described later pass through the grooves 23c. Therefore, it is possible to assemble the movable member 3 smoothly with respect to the fixing member main body 20. In addition, the object-side thick portion 22 and the image-side thick portion 23 may be formed separately from the cylinder 21, and then, object-side thick portion and the image-side thick portion may be attached to the cylinder 21 at the time of assembly.

Figure 6A:
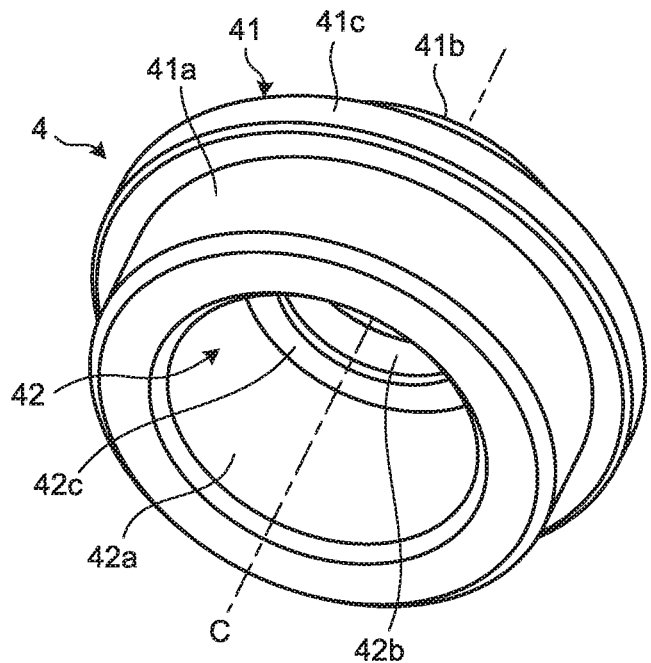
FIG. 6A is a perspective view illustrating a configuration of a front frame portion of the optical unit according to the first embodiment of the disclosure.
Figure 6B:
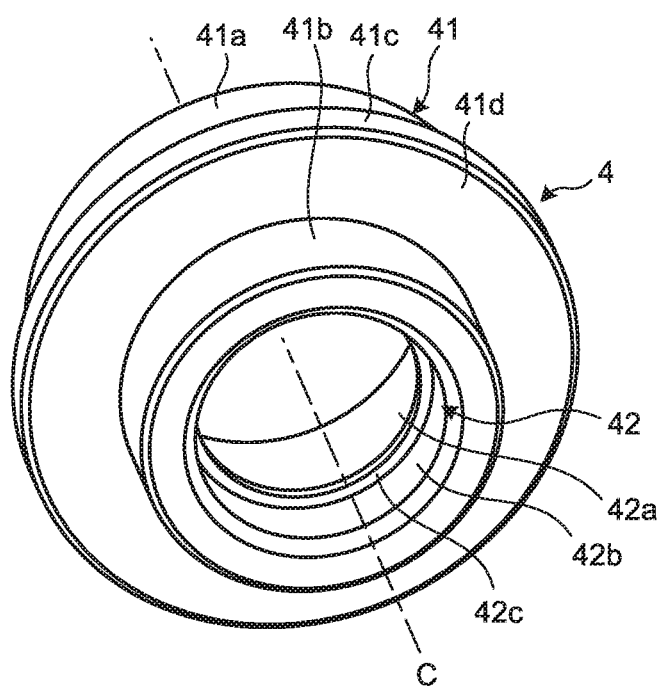
FIG. 6B is a perspective view illustrating a configuration of the front frame portion of the optical unit according to the first embodiment of the disclosure as viewed from the side opposite to that of FIG. 6A.

FIGS. 6A and 6B are perspective views illustrating a configuration of the front frame portion 4 as perspective views viewed from different sides of the axis C. In addition, the central axis of the front frame portion 4 is referred to as the axis C because the central axis of the front frame portion coincides with the central axis of the fixing member main body 20 at the time of assembly. The front frame portion 4 is a cylindrical member having an outer peripheral portion 41 and an inner peripheral portion 42. The outer peripheral portion 41 has a first outer peripheral portion 41a, a second outer peripheral portion 41b, and an outer peripheral side protrusion 41c. The inner peripheral portion 42 has a first inner peripheral portion 42a, a second inner peripheral portion 42b, and an inner peripheral side protrusion 42c.

In the outer peripheral portion 41, the first outer peripheral portion 41a is larger in diameter than the second outer peripheral portion 41b. Between the first outer peripheral portion 41a and the second outer peripheral portion 41b, the outer peripheral side protrusion 41c protruding on the radial-direction outer side with the largest diameter is provided.

In the inner peripheral portion 42, the first inner peripheral portion 42a is larger in diameter than the second inner peripheral portion 42b. Between the first inner peripheral portion 42a and the second inner peripheral portion 42b, the inner peripheral side protrusion 42c protruding on the radial-direction inner side with the smallest diameter is located.

The front frame portion 4 retains the object-side fixed lens group Gf. The object-side fixed lens group Gf has a front first lens Lf1 and a front second lens Lf2, which are arranged in this order from the object side. The first inner peripheral portion 42a retains the front first lens Lf1, and the second inner peripheral portion 42b retains the front second lens Lf2. As illustrated in FIGS. 3 and 4, it is preferable that the image side of the front first lens Lf1 and the object side of the front second lens Lf2 are in contact with the inner peripheral side protrusion 42c.

In the insertion of the front frame portion 4 into the fixing member main body 20, while the second outer peripheral portion 41b is brought into contact with an inner peripheral surface 22a of the object-side thick portion 22 of the fixing member main body 20, the front frame portion is inserted until an object-side end surface 22b of the fixing member main body 20 comes into contact with a stepped portion 41d between the second outer peripheral portion 41b and the outer peripheral side protrusion 41c.

Figure 7A:
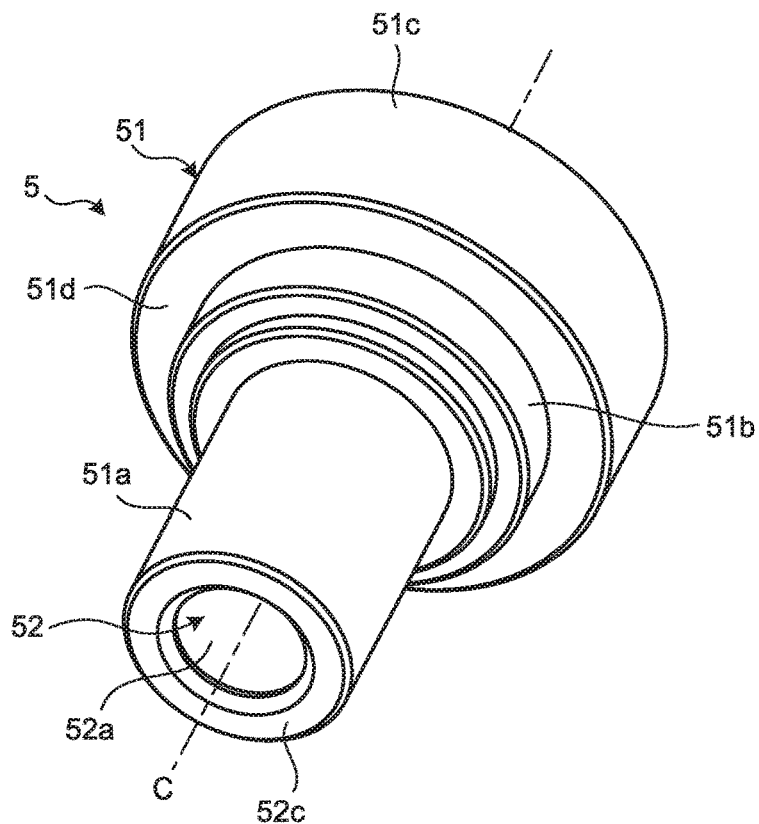
FIG. 7A is a perspective view illustrating a configuration of a rear frame portion of the optical unit according to the first embodiment of the disclosure.
Figure 7B:
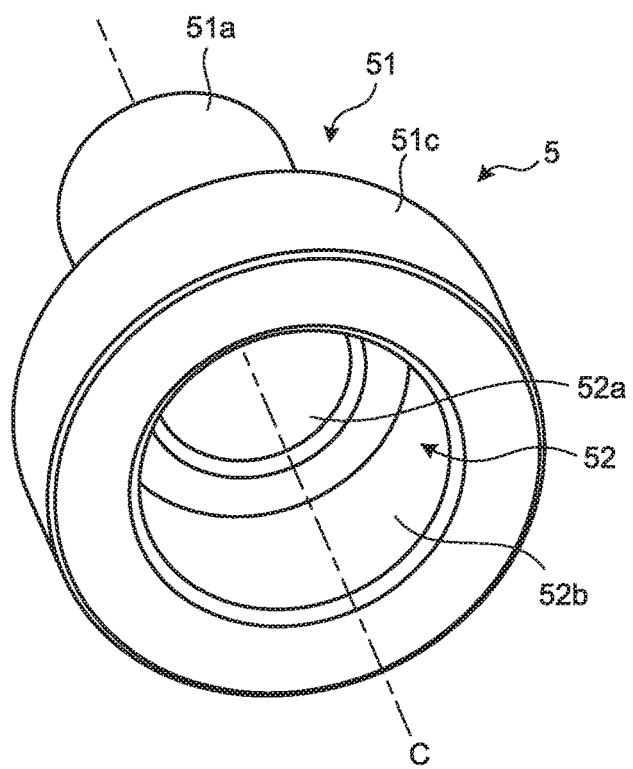
FIG. 7B is a perspective view illustrating a configuration of the rear frame portion of the optical unit according to the first embodiment of the disclosure as viewed from the side opposite to that of FIG. 7A.

FIGS. 7A and 7B are perspective views illustrating a configuration of the rear frame portion 5 as perspective views respectively viewed from different sides of the axis C. In addition, similarly to the front frame portion 4, the central axis of the rear frame portion 5 is referred to as the axis C because the central axis of the rear frame portion coincides with the central axis of the fixing member main body 20 at the time of assembly. The rear frame portion 5 is a cylindrical member having an outer peripheral portion 51 and an inner peripheral portion 52. The outer peripheral portion 51 has a first outer peripheral portion 51a, a second outer peripheral portion 51b, and a third outer peripheral portion 51c. The inner peripheral portion 52 has a first inner peripheral portion 52a, a second inner peripheral portion 52b, and an inner peripheral side protrusion 52c.

In the outer peripheral portion 51, the first outer peripheral portion 51a is smaller in diameter than the second outer peripheral portion 51b, and the second outer peripheral portion 51b is smaller in diameter than the third outer peripheral portion 51c.

In the inner peripheral portion 52, the first inner peripheral portion 52a is smaller in diameter than the second inner peripheral portion 52b. On the object-side end portion of the first inner peripheral portion 52a, the inner peripheral side protrusion 52c protruding on the radial-direction inner side with the smallest diameter is provided.

The rear frame portion 5 retains the image-side fixed lens group Gb. The image-side fixed lens group Gb has a rear first lens Lb1 and a rear second lens Lb2. The first inner peripheral portion 52a retains the rear first lens Lb1 and the rear second lens Lb2 in this order from the object side. As illustrated in FIGS. 3 and 4, it is preferable that the object side of the rear first lens Lb1 is in contact with the inner peripheral side protrusion 52c.

In the insertion of the rear frame portion 5 into the fixing member main body 20, while the second outer peripheral portion 51b is brought into contact with the fixed-side sliding surface 24 of the image-side thick portion 23 of the fixing member main body 20, the rear frame portion is inserted until an image-side end surface 23a of the fixing member main body 20 comes into contact with a stepped portion 51d between the second outer peripheral portion 51b and the third outer peripheral portion 51c.

The fixing member 2 having the above structure is made of, for example, a non-magnetic material having a relative permeability of larger than 1.0. As such a material, there may be exemplified an austenitic stainless steel.

Figure 8:
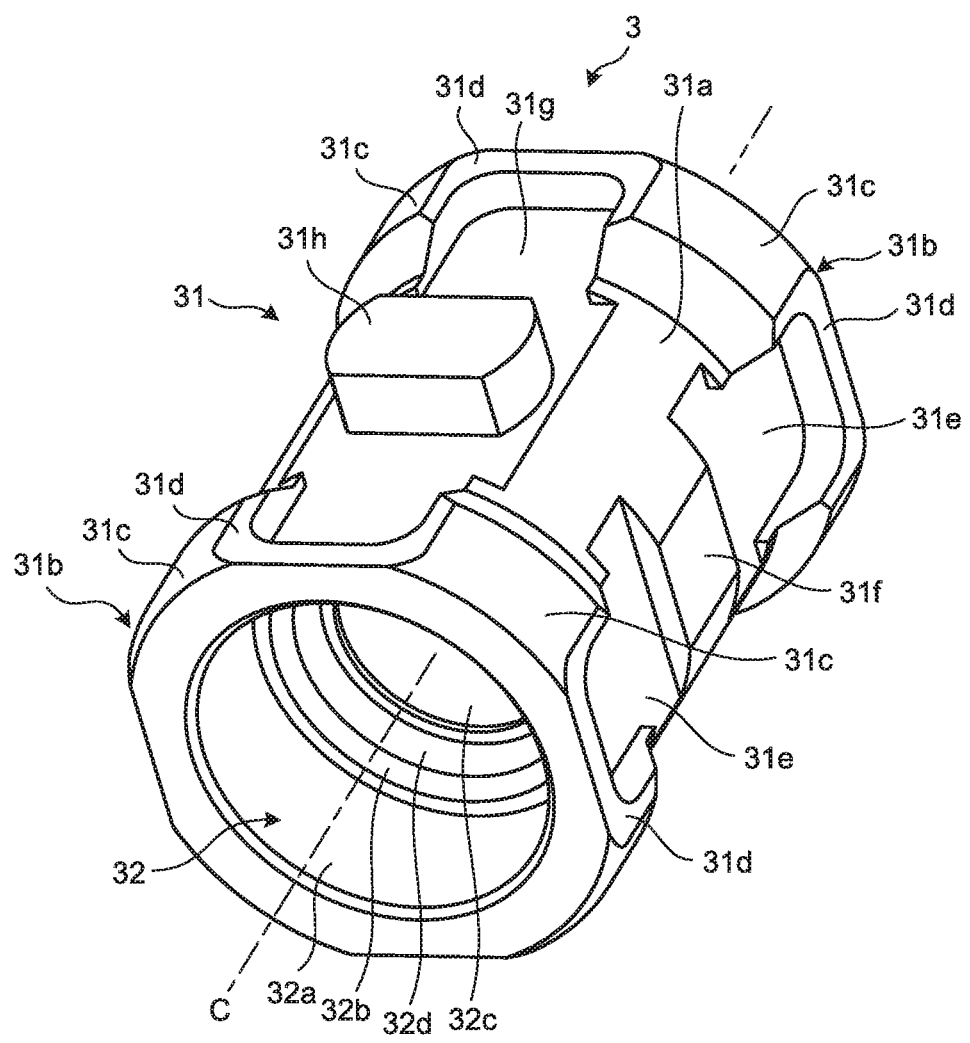
FIG. 8 is a perspective view illustrating a configuration of a movable member of the optical unit according to the first embodiment of the disclosure.

FIG. 8 is a perspective view illustrating a configuration of the movable member 3. The movable member 3 illustrated in the figure is configured with a cylindrical member having an outer peripheral portion 31 and an inner peripheral portion 32. Hereinafter, the central axis of the movable member 3 is also referred to as an axis C. This is because the central axis of the movable member 3 coincides with the central axis of the fixing member main body 20 during assembly.

The outer peripheral portion 31 has a cylinder 31a and two protruding edge portions 31b which are respectively formed on both end portions of the cylinder 31a in the direction of the axis C and are larger in outer diameter than the cylinder 31a. The cylinder 31a and the protruding edge portion 31b may be formed as an integral member or as separate members.

The protruding edge portion 31b has movable-side sliding surfaces 31c configured with an outer peripheral surface thereof and planar portions 31d formed on portions of the radial-direction outer side of the protruding edge portion 31b. In the case illustrated in FIG. 8, the protruding edge portion 31b alternately has four movable-side sliding surfaces 31c and four planar portions 31d at equal intervals along the peripheral direction around the axis C. The planar portions 31d pass through the same plane as any of the four planar portions 31d formed on the other end side along the direction of the axis C. In other words, the outer peripheral portion 31 has four sets of two planar portions 31d which are formed at different end portions and pass through the same plane.

Between the three sets of planar portions 31d of the four sets of planar portions 31d, step difference portions 31e formed radially inward from the cylinder 31a and having a planar outer peripheral surface are provided, respectively. A cutout portion 31f is provided at the central portion of the step difference portion 31e formed between the three sets of planar portions 31d in the direction of the axis C by cutting out the surface of the cylinder 31a to form a planar outer periphery.

A step difference portion 31g formed on the radial-direction inner side from the cylinder 31a and having a planar outer peripheral surface is also provided between the remaining one set of planar portions 31d among the four sets of planar portions 31d. A rotation restricting member 31h which restricts rotation of the movable member 3 around the axis C is provided at the central portion of the step difference portion 31g in the direction of the axis C so as to protrude from the outer peripheral surface of the step difference portion 31g. Among the side surfaces of the rotation restricting member 31h, the side surfaces which are in contact with the fixing member 2 have curved R shapes, and the side surfaces facing the first magnet 12a and the second magnet 12b have planar shapes. In other words, among the surfaces of the rotation restricting member 31h, the surfaces parallel to the axis C have a shape in which a circle is shaped by cutting out the object side and the image side of the axis C with straight lines in a direction perpendicular to the direction of the axis C (D-cut) and has a shape surrounded by two arcs and two straight lines. In addition, the surface of the rotation restricting member may have a circular shape of which diameter is the length of the rotation restricting member 31h in the direction of the axis C illustrated in FIG. 8. In addition, the surface of the rotation restricting member may have a rectangular shape.

As illustrated in FIG. 2, the peripheral-direction width of the plane of the rotation restricting member 31h perpendicular to the axis C is larger than the peripheral-direction width of the magnet 12 (the second magnet 12b is illustrated in FIG. 2) in the same plane.

The inner peripheral portion 32 has a first inner peripheral portion 32a, a second inner peripheral portion 32b, a third inner peripheral portion 32c, and an inner peripheral side protrusion 32d. The second inner peripheral portion 32b is smaller in diameter than the first inner peripheral portion 32a and the third inner peripheral portion 32c. Between the second inner peripheral portion 32b and the third inner peripheral portion 32c, the inner peripheral side protrusion 32d protruding on the radial-direction inner side with the smallest diameter is provided.

The movable member 3 retains the movable lens group Gv. Specifically, the second inner peripheral portion 32b of the movable member 3 retains a movable first lens Lv1 included in the movable lens group Gv. As illustrated in FIG. 3 and FIG. 4, it is preferable that the image side of the movable first lens Lv1 is in contact with the inner peripheral side protrusion 32d.

The movable member 3 is inserted into the fixing member main body 20 while the movable-side sliding surface 31c is in contact with the fixed-side sliding surface 24. In addition, as illustrated in FIGS. 3 and 4, the movable member 3 is inserted such that the first outer peripheral portion 51a of the rear frame portion 5 faces the radial-direction inner side of the third inner peripheral portion 32c. Thus, at least a portion of the image-side fixed lens group Gb is located on the radial-direction inner side of the third inner peripheral portion 32c of the movable member 3. In the first embodiment, when the movable member 3 is moved to the most object-side position, at least a portion of the object-side fixed lens group Gf is located on the radial-direction inner side of the first inner peripheral portion 32a of the movable member 3.

The movable member 3 having the above structure is made of a material such as a stainless steel, aluminum, or a resin.

In the optical unit 1, as illustrated in FIG. 4, in the direction along the axis C, a distance L1 from the most object-side position to the most image-side position on the movable-side sliding surface 31c of the movable member 3 is larger than a distance L2 from the light emitting surface of the object-side fixed lens group Gf retained by the front frame portion 4 to the incident surface of the image-side fixed lens group Gb retained by the rear frame portion 5 (L1>L2). In addition, the distance from the most object-side position to the most image-side position of the movable-side sliding surface 31c of the movable member 3 does not include a chamfered portion.

Next, a configuration of the voice coil motor 10 will be described. As illustrated in FIG. 3, the voice coil motor 10 has coils 11 arranged in the fixing member main body 20 of the fixing member 2, and magnets 12 arranged in the movable member 3 so as to face the coils 11.

As illustrated in FIGS. 3 and 4, the coils 11 are configured to include a first coil 11a wound around the outer periphery of the cylinder 21 of the fixing member main body 20 and a second coil 11b arranged side by side along the direction of the axis C of the first coil 11a and wound around the outer periphery of the cylinder 21 of the fixing member main body 20. In addition, the coils 11 wound in advance may be arranged later. It is preferable that the first coil 11a and the second coil 11b that are adjacent to each other along the axis C direction are connected in series, but they may be connected in parallel.

As illustrated in FIGS. 3 and 4, the first coil 11a and the second coil 11b have planar portions 11ap and 11bp that face the recessed portions 21a of the fixing member main body 20, respectively. In addition, the first coil 11a and the second coil 11b have cylinders 11at and 11bt that face the cylinder 21, respectively. In the first coil 11a, in the cross section perpendicular to the axis C, the four planar portions hap and the four cylinders 11at are alternately arranged. Similarly, in the second coil 11b, in the cross section perpendicular to the axis C, the four planar portions 11bp and the four cylinders 11bt are alternately arranged (refer to FIG. 2).

As illustrated in FIGS. 1 to 4, the magnets 12 include four first magnets 12a and four second magnets 12b that face the planar portions 11ap and 11bp, respectively, on the inner sides of the planar portion hap of the first coil 11a and the planar portion 11bp of the second coil 11b and are arranged side by side in the direction of the axis C. The four sets of first magnet 12a and second magnet 12b aligned along the direction of the axis C are arranged at equal intervals every 90° along the peripheral direction in a cross section perpendicular to the axis C. The rotation restricting member 31h is positioned between one set of the first magnet 12a and the second magnet 12b among the four sets. By employing such an arrangement, it is possible to install the first magnet 12a and the second magnet 12b to be stable. As a result, a stable magnetic field is formed in the voice coil motor 10, and it is possible to suppress the shake of the movable member 3 moving with respect to the fixing member 2. In the first embodiment, the magnets 12 are installed every 90° about the axis C, but the magnets 12 may be installed at other angular intervals.

As illustrated in FIGS. 3 and 4, the sum of widths of the first magnet 12a and the second magnet 12b in the direction of the axis C is shorter than the sum of widths of the first coil 11a and the second coil 11b in the direction of the axis C. Thus, the first magnet 12a and the second magnet 12b may be allowed to always exist within the widths of the first coil 11a and the second coil 11b in the direction of the axis C, respectively, in the range of movement of the movable member 3.

Figure 9:
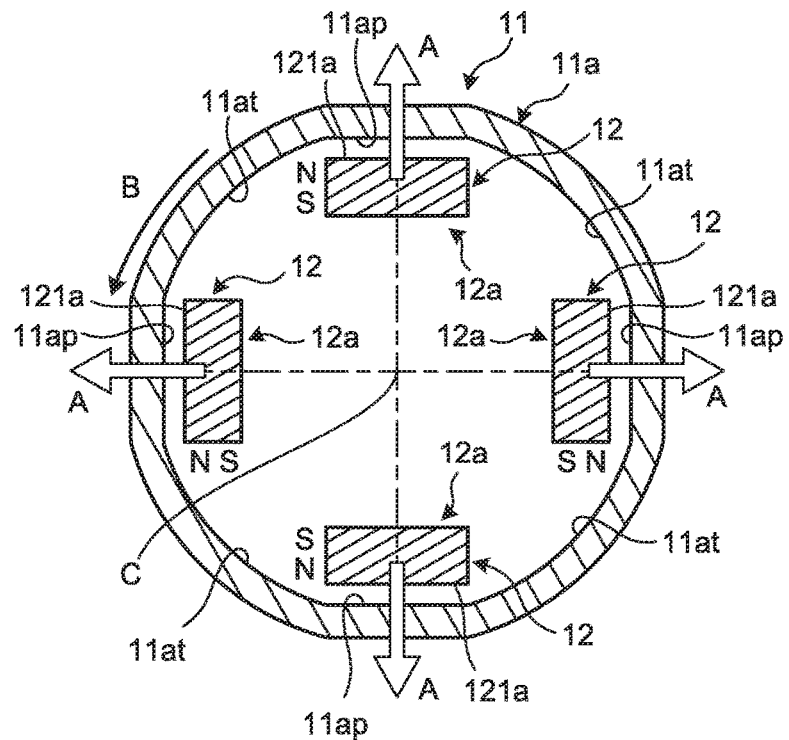
FIG. 9 is a view illustrating a configuration of only a voice coil motor as viewed in a cross section taken along line IV-IV illustrated in FIG. 3.
Figure 10:
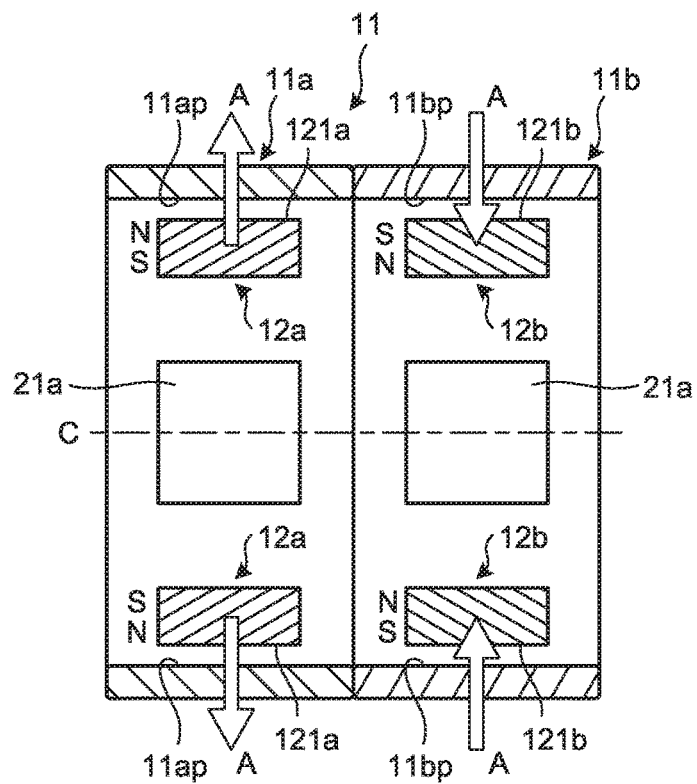
FIG. 10 is a view illustrating only the voice coil motor in the same cross section as FIG. 3.

FIG. 9 is a view illustrating the configuration of only the voice coil motor as viewed in a cross section taken along line IV-IV illustrated of FIG. 3. FIG. 10 is a view illustrating only the voice coil motor in the same cross section as FIG. 3.

As illustrated in FIGS. 9 and 10, the first magnet 12a and the second magnet 12b which are paired in the direction of the axis C are arranged to be separated from each other. The set of the first magnets 12a and the set of the second magnets 12b are magnetized in the radial direction, and the magnetic poles are opposite to each other. In the cases illustrated in FIGS. 9 and 10, the first magnet 12a has the N pole on the side of the first coil 11a and the S pole on the opposite side thereof, and the second magnet 12b has the S pole on the side of the second coil 11b and the N pole on the opposite side thereof. In this case, the magnetic polarization directions of the first magnet 12a and the second magnet 12b are perpendicular to the axis C as illustrated by hollow arrows A in FIGS. 9 and 10. In addition, more generally, the magnetic polarization directions of the first magnet 12a and the second magnet 12b may be directions crossing the axis C.

In the first embodiment, it is preferable that the winding direction of the coil 11 is reversed between the set of the first magnets 12a and the set of the second magnets 12b. For example, as illustrated in FIG. 9, when the first coil 11a is wound in the direction of the arrow B, the second coil 11b may be wound in the opposite direction. Alternatively, the winding directions of the first coil 11a and the second coil 11b may be the same, and the first coil 11a and the second coil 11b may be connected so that the current directions are reversed. In this case, as illustrated in FIG. 9, when a current in the direction of the arrow B is applied to the first coil 11a, a current may flow in the second coil 11b in the direction opposite to the arrow B.

In the optical unit 1 having the above configuration, the movable member 3 in which the first magnet 12a is installed so as to face the first coil 11a is arranged on the radial-direction inner side of the fixing member main body 20 around which the first coil 11a is wound. Therefore, the planar portion hap of the first coil 11a exists in a magnetic field in a direction perpendicular to a radial-direction outer surface 121a of the first magnet 12a. In addition, the second magnet 12b is configured in a similar manner. Therefore, the driving efficiency is improved, and the movable member 3 may be quickly moved. In addition, the radial-direction outer surface 121a of the first magnet 12a and a radial-direction outer surface 121b of the second magnet 12b are configured to have a planar shape, so that it is possible to easily assemble the optical unit 1.

In addition, when a current is allowed to flow in the coil 11 of the optical unit 1, a force in the direction of the axis C is generated in the movable member 3 due to the influence of the magnetic field of the magnet 12, and the movable member 3 is moved in the direction of the axis C with respect to the fixing member 2. For example, by controlling the currents respectively flowing in the first coil 11a and the second coil 11b, the movable member 3 may be moved with respect to the fixing member 2. Even in a state where the movable member 3 is being moved with respect to the fixing member 2, the radial-direction outer surface of the magnet 12 is arranged in the recessed portion 21a of the fixing member main body 20.

In addition, in the optical unit 1, as illustrated in FIG. 4, the outer peripheral surface of the protruding edge portion 31b of the movable member 3 constitutes the movable-side sliding surface 31c which is to be in contact with the fixed-side sliding surface 24 of the fixing member main body 20. By bringing the fixed-side sliding surface 24 of the fixing member main body 20 and the movable-side sliding surface 31c of the movable member 3 into contact with each other, it is possible to always move the movable member 3 in contact with the fixing member main body 20, it is possible to suppress the inclination of the movable member 3 with respect to the fixing member 2, and it is possible to accurately move the movable member 3.

According to the first embodiment of the disclosure described above, the coil 11 arranged in the fixing member 2 and the magnet 12 arranged on the movable member 3 and magnetically polarized in the direction perpendicular to the central axis C are provided, and the voice coil motor 10 capable of relatively moving the movable member 3 with respect to the fixing member along the direction of the central axis C and the rotation restricting member 31h for restricting rotation of the movable member 3 about the central axis C with respect to the fixing member 2 are included, so that it is possible to improve the driving efficiency, and it is possible to quickly operate the movable member 3. In addition, during the operation of the movable member 3, the fixed-side sliding surface 24 of the fixing member main body 20 and the movable-side sliding surface 31c of the movable member 3 come into contact with each other, so that it is possible to suppress the inclination of the movable member 3 with respect to the fixing member 2, and it is possible to accurately move the movable member 3. Therefore, it is possible to realize miniaturization and weight reduction of the actuator for moving a movable lens forward and backward.

In addition, according to the first embodiment, since the rotation restricting member 31h is provided, even in the case where the fixing member 2 is made of a material having a magnetic property, for example, it is possible to prevent the magnet 12 of the movable member 3 and the fixing member 2 from being adsorbed. As a result, an increase in the amount of force for driving the movable member 3 by the adsorption between the magnet 12 and the fixing member 2 may be suppressed, so that it is possible to reliably realize the miniaturization and weight reduction of the voice coil motor 10.

In addition, according to the first embodiment, the fixing member 2 is configured by using the fixing member main body 20, the front frame portion 4, and the rear frame portion 5, so that it is possible to reduce the number of parts and the number of assembling steps and to increase a degree of freedom in design, and it is possible to realize the cost reduction.

In addition, according to the first embodiment, since the coil 11 is wound around the axis C, the sliding axis of the movable member 3 and the action axis of the driving force generated by the voice coil motor 10 are the same, so that it is possible to drive with stability.

In addition, according to the first embodiment, since the fixed-side sliding surface 24 of the fixing member 2 is formed to be divided in the peripheral direction, it is possible to miniaturize the optical unit 1 with a simple structure.

In addition, according to the first embodiment, since a plurality of magnets 12 are arranged symmetrically with respect to the axis C, it is possible to stably increase the driving force.

According to the first embodiment, the magnet 12 has a plurality of sets of the first magnet 12a and the second magnet 12b which are adjacent to each other along the direction of the axis C and of which magnetic polarization directions are opposite to each other, and a plurality of the first magnets 12a have the same magnetic polarization direction. The coil 11 has first coils 11a facing a plurality of the first magnets 12a and second coils 11b facing a plurality of the second magnets 12b and connected to the first coil 11a, and the first coils 11a and the second coils 11b may increase the driving force since the current flowing directions of the first coil 11a and the second coil 11b are opposite to each other.

Second Embodiment

Figure 11:
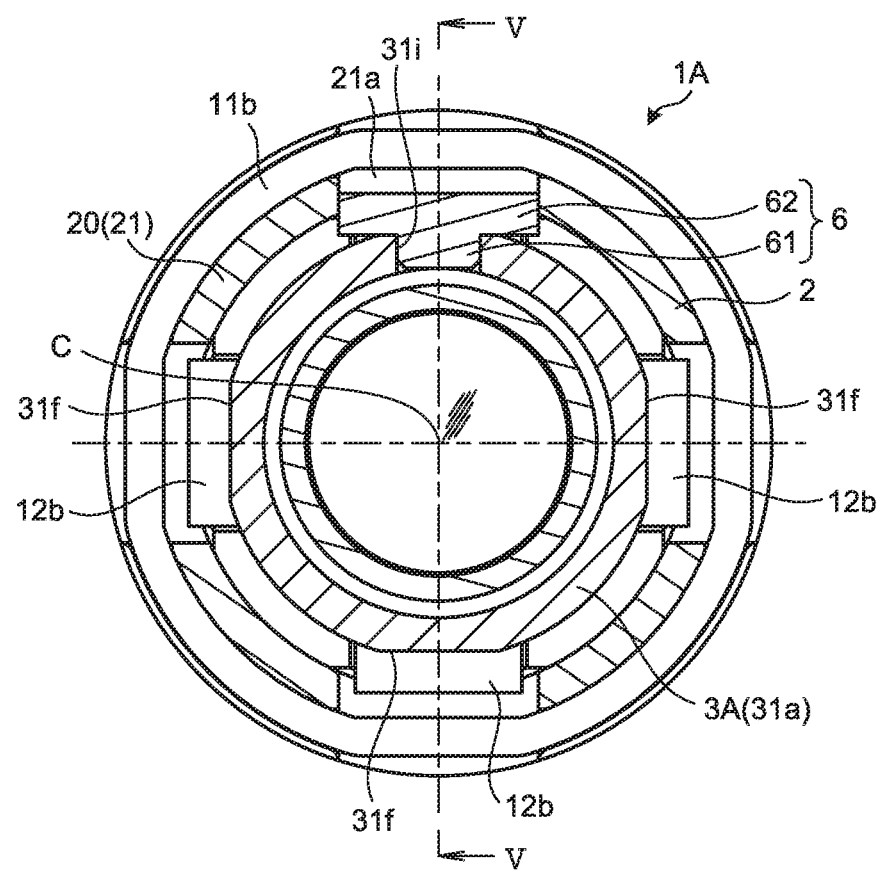
FIG. 11 is a cross-sectional view illustrating a configuration of main components of an optical unit according to a second embodiment of the disclosure.
Figure 12:
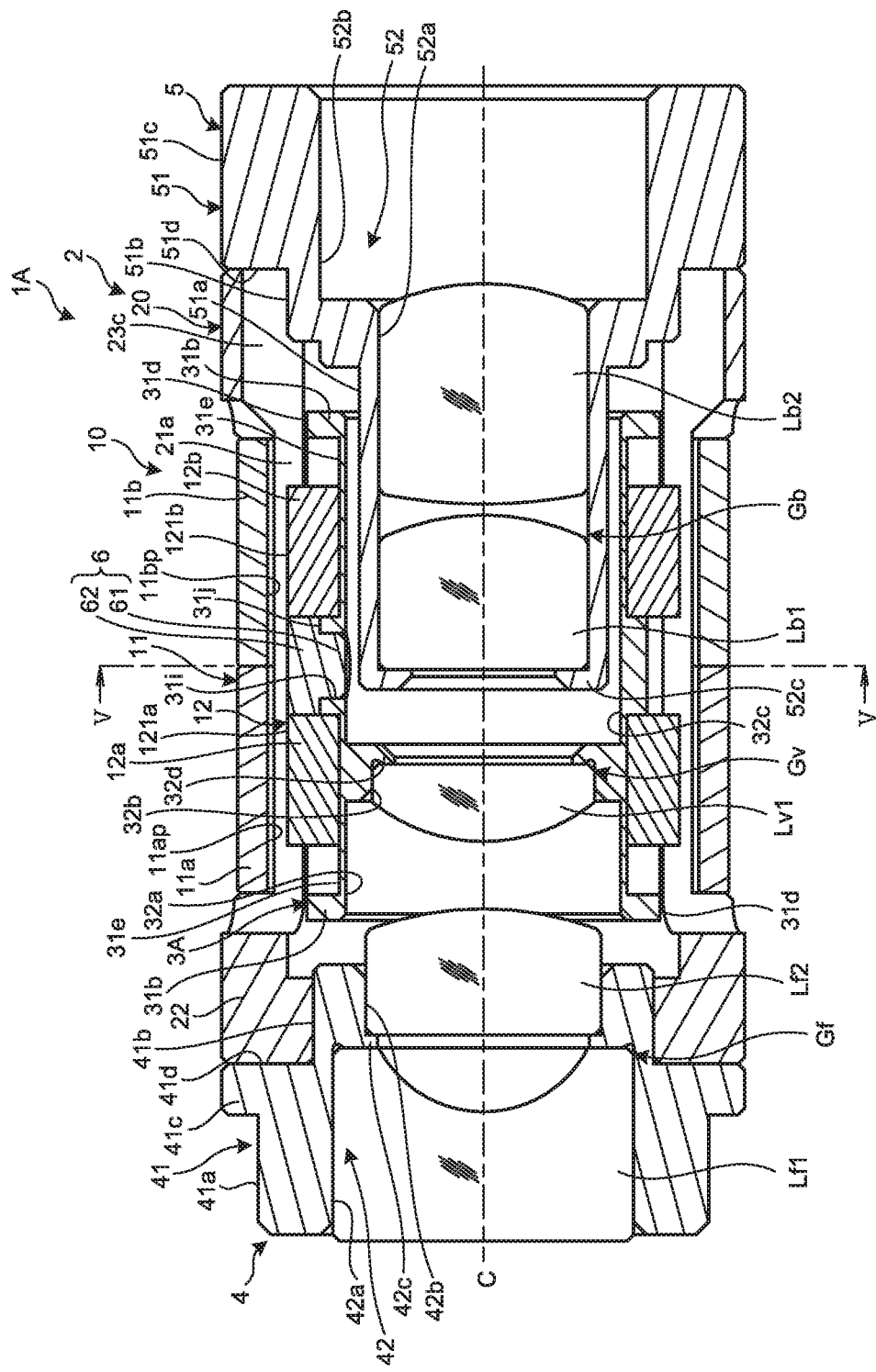
FIG. 12 is a cross-sectional view of the optical unit as viewed in a cross section taken along line V-V of FIG. 11.

FIG. 11 is a cross-sectional view illustrating a configuration of main components of an optical unit according to a second embodiment of the disclosure. FIG. 12 is a cross-sectional view of the optical unit as viewed in a cross section taken along line V-V of FIG. 11. An optical unit 1A illustrated in FIGS. 11 and 12 is configured to include a fixing member 2, a movable member 3A, a voice coil motor 10, and a rotation restricting member 6 attached to the movable member 3A. In the second embodiment, components having the same configurations as those in the first embodiment will be described by using the same reference numerals as those in the first embodiment.

Figure 13:
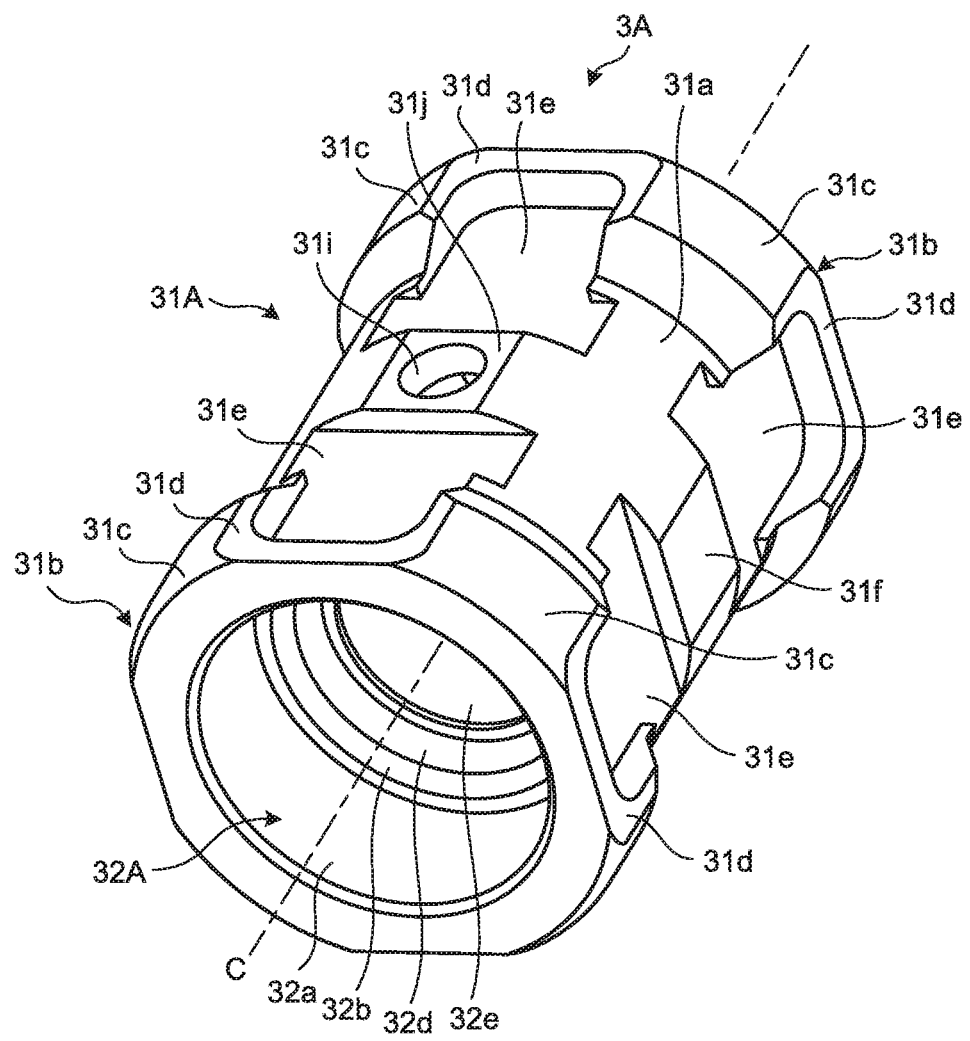
FIG. 13 is a perspective view illustrating a configuration of a movable member of the optical unit according to the second embodiment of the disclosure.

FIG. 13 is a perspective view illustrating a configuration of a movable member 3A. As illustrated in FIG. 13, the movable member 3A is configured with a cylindrical member having an outer peripheral portion 31A and an inner peripheral portion 32A.

The outer peripheral portion 31A has a cylinder 31a and a protruding edge portion 31b. The protruding edge portion 31b has a movable-side sliding surface 31c and a planar portion 31d.

In the case illustrated in FIG. 13, the protruding edge portion 31b alternately has four movable-side sliding surfaces 31c and four planar portions 31d at equal intervals along the peripheral direction around the axis C. The planar portion 31d passes through the same plane as any of the four planar portions 31d formed on the other end side along the direction of the axis C. In other words, the outer peripheral portion 31A has four sets of two planar portions 31d which are formed at different end portions and pass through the same plane. Between the four sets of planar portions 31d, step difference portions 31e are provided, respectively. A cutout portions 31f is provided at the central portion of the step difference portion 31e in the direction of the axis C formed between the three sets of planar portions 31d among the four sets of planar portions 31d by cutting out the surface of the cylinder 31a to form a planar outer periphery.

At the central portions of a step difference portions 31e in the direction of the axis C formed between the remaining set of planar portions 31d among the four sets of planar portions 31d, a retaining portion 31j for retaining the rotation restricting member 6 is provided by cutting out the surface of the cylinder 31a to form a planar portion where the outer periphery is planar and forming a hole portion 31i passing through the planar portion in the radial direction. In addition, the hole portion 31*i* may have a shape having the bottom on the radial-direction inner peripheral side of the outer peripheral portion 31A.

The inner peripheral portion 32A of the movable member 3 has a first inner peripheral portion 32*a*, a second inner peripheral portion 32*b*, a third inner peripheral portion 32*e*, and an inner peripheral side protrusion 32*d*. An opening of the hole portion 31*i* is formed in the third inner peripheral portion 32*e*.

Figure 14:
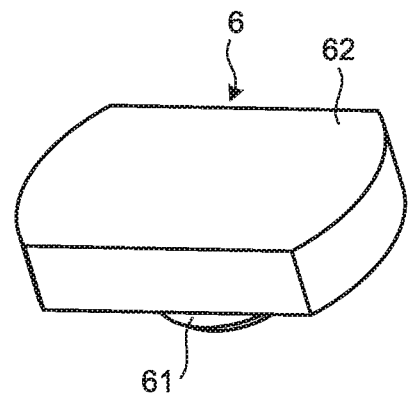
FIG. 14 is a perspective view illustrating a configuration of a rotation restricting member of the optical unit according to the second embodiment of the disclosure.

FIG. 14 is a perspective view illustrating a configuration of the rotation restricting member 6. The rotation restricting member 6 is configured to include a cylindrical insertion portion 61 having a diameter that allows insertion into the hole portion 31*i* of the movable member 3A and a head portion 62 which is provided at one end of the insertion portion 61 in the height direction and mounted on an outer peripheral side surface of the retaining portion 31*j* while passing through the insertion portion 61 through the hole portion 31*i* and protrudes from the retaining portion 31*j* toward the outer periphery in the radial direction. The portion of the side surface of the head portion 62 which is in contact with the fixing member 2 has a curved R shape while the side surfaces facing the first magnet 12*a* and the second magnet 12*b* have planar shapes. The rotation restricting member 6 is fixedly adhered to the movable member 3A by adhesion or the like while being retained by the retaining portion 31*j*. In addition, the surface shape of the rotation restricting member parallel to the axis C in a state of being fixedly adhered to the movable member 3A may have a circular shape or a rectangular shape.

As illustrated in FIG. 11, the peripheral-direction width of the plane of the head portion 62 of the rotation restricting member 6 perpendicular to the axis C is larger than the peripheral-direction width of the magnet 12 (the second magnet 12*b* is described in FIG. 11) in the same plane.

According to the second embodiment of the disclosure described above, it is possible to obtain the same effects as those of the above-described first embodiment.

In addition, according to the second embodiment, the movable member 3A and the rotation restricting member 6 are formed separately, so that it is possible to further facilitate machining of the movable member 3A and the rotation restricting member 6.

Third Embodiment

Figure 15:
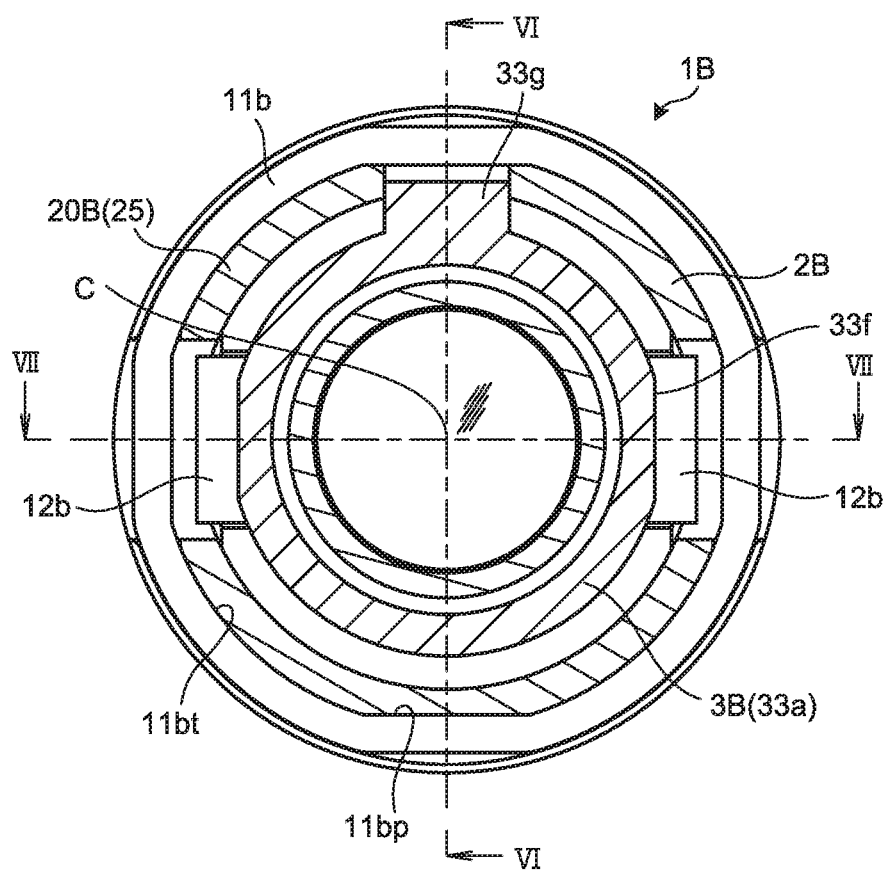
FIG. 15 is a cross-sectional view illustrating a configuration of main components of an optical unit according to a third embodiment of the disclosure.
Figure 16:
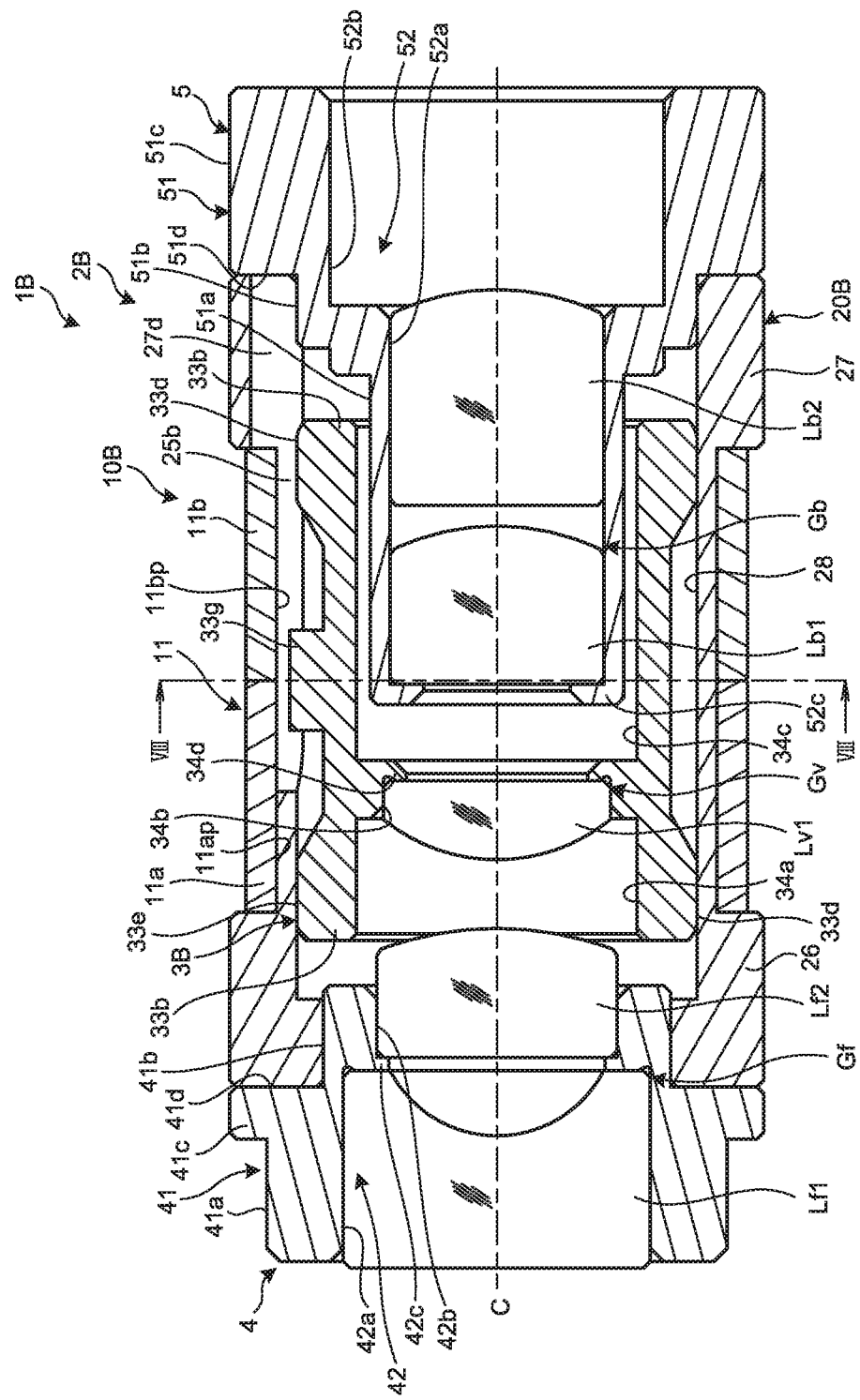
FIG. 16 is a cross-sectional view of the optical unit as viewed in a cross section taken along line VI-VI of FIG. 15.
Figure 17:
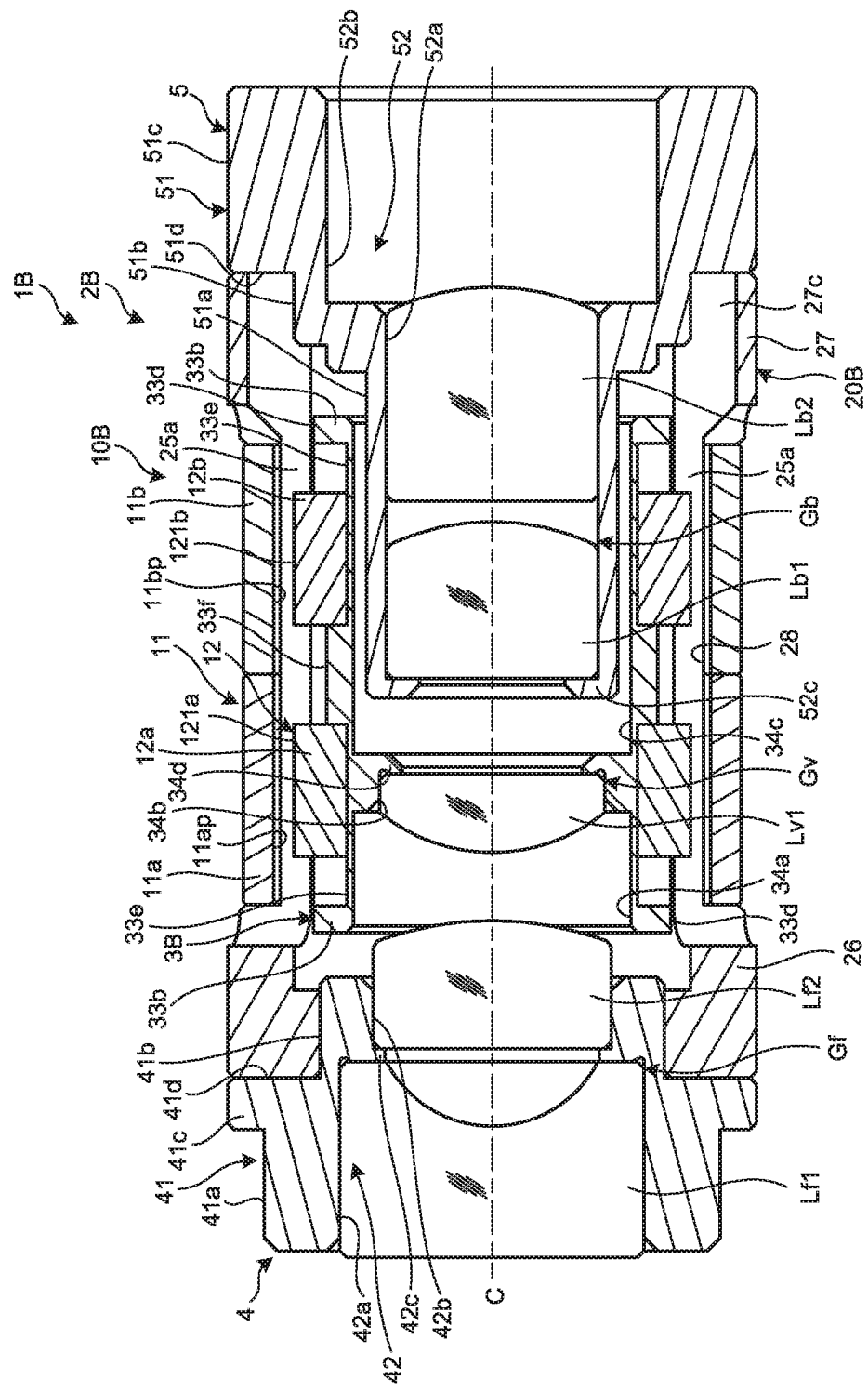
FIG. 17 is a cross-sectional view of the optical unit as viewed in a cross section taken along line VII-VII of FIG. 15.

FIG. 15 is a cross-sectional view illustrating a configuration of main components of an optical unit according to a third embodiment of the disclosure. FIG. 16 is a cross-sectional view of the optical unit as viewed in a cross section taken along line VI-VI of FIG. 15. FIG. 17 is a cross-sectional view of the optical unit as viewed in a cross section taken along line VII-VII of FIG. 15. FIG. 15 is a cross-sectional view of the optical unit as viewed in a cross section taken along line VIII-VIII of FIG. 16.

An optical unit 1B illustrated in FIGS. 15 to 17 is configured to include a fixing member 2B, a movable member 3B, and a voice coil motor 10B. In the third embodiment, components having the same configurations as those in the first embodiment will be described by using the same reference numerals as those in the first embodiment.

Figure 18:
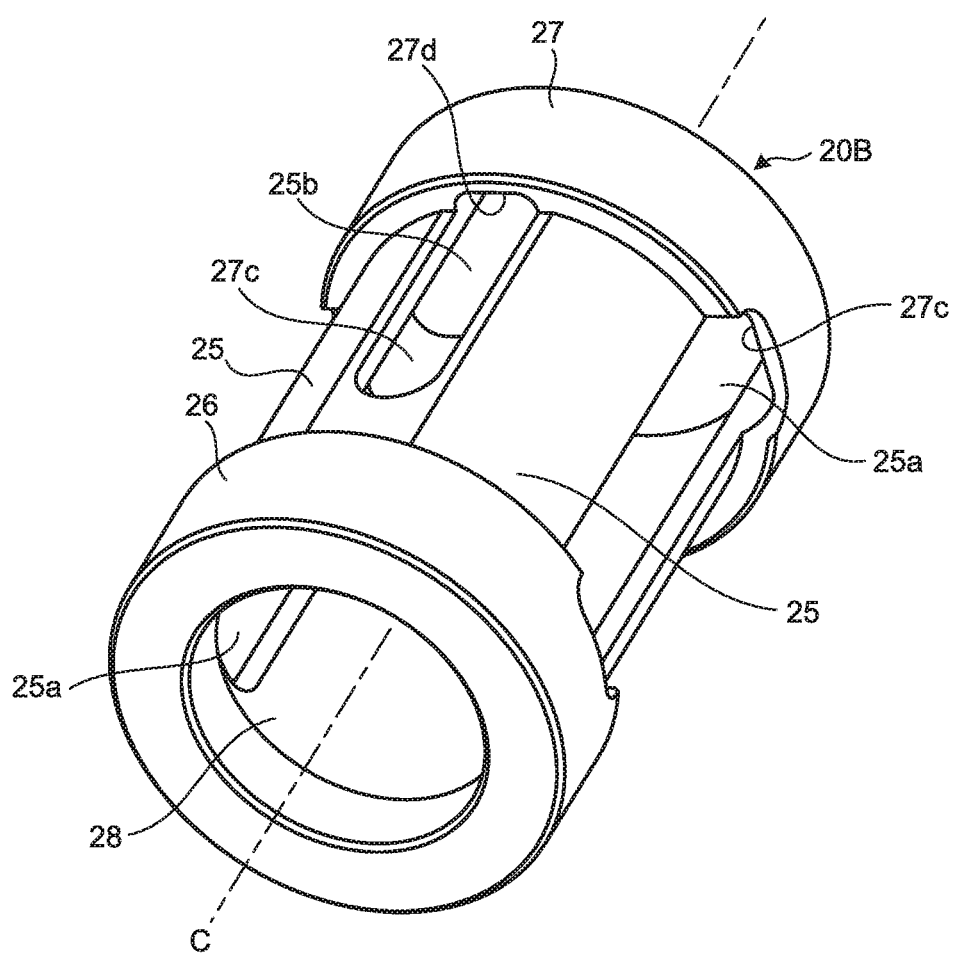
FIG. 18 is a perspective view illustrating a configuration of a fixing member main body of the optical unit according to the third embodiment of the disclosure.

FIG. 18 is a perspective view illustrating a configuration of a fixing member main body 20B included in the fixing member 2B. The fixing member main body 20B illustrated in the figure is configured with a cylindrical member centered on a predetermined axis C. The fixing member main body 20B is configured to include a cylinder 25 having the axis C as a central axis, an object-side thick portion 26 formed on the object side in the direction of the axis C with respect to the cylinder 25, and an image-side thick portion 27 formed on the image side in the direction of the axis C with respect to the cylinder 25.

In the cylinder 25, two first recessed portions 25*a* and one second recessed portion 25*b* are formed. Specifically, the two first recessed portions 25*a* are formed at positions 180° rotationally symmetrical with respect to the axis C, and the second recessed portion 25*b* is formed at the position rotated by 90° around the axis C from the two first recessed portions 25*a*. The surface on the radial-direction inner side of the cylinder 25 excluding the first recessed portions 25*a* and the second recessed portion 25*b* is a cylindrical surface and is a fixed-side sliding surface 28 for guiding and supporting the movable member 3B. The fixed-side sliding surface 28 has a shape divided in the peripheral direction by the first recessed portions 25*a* and the second recessed portion 25*b*. The second recessed portion 25*b* is formed up to the middle of the cylinder 25 along the axis C direction. As illustrated in FIG. 16, this is because, in the case of the third embodiment, the magnets 12 are not arranged on both sides of the rotation restricting member 33*g* in the direction of the axis C, and thus, there is no need to recess the whole of the cylinder 25 along the direction of the axis C.

The object-side thick portion 26 is formed so as to protrude radially outward and radially inward from the cylinder 25. The image-side thick portion 27 is formed so as to protrude radially outward from the cylinder 25. On the fixed-side sliding surface 28 on the radial-direction inner side of the image-side thick portion 27, first grooves 27*c* through which the magnets 12 pass at the time of assembling the movable member 3B are formed. In addition, on the fixed-side sliding surface 28 on the radial-direction inner side of the image-side thick portion 27, second grooves 27*d* through which the rotation restricting member 33*g* pass at the time of assembling the movable member 3B are formed. Therefore, it is possible to smoothly assemble the movable member 3B with respect to the fixing member main body 20B. In addition, the object-side thick portion 26 and the image-side thick portion 27 may be formed separately from the cylinder 25 and attached to the cylinder 25 at the time of assembly.

Figure 19:
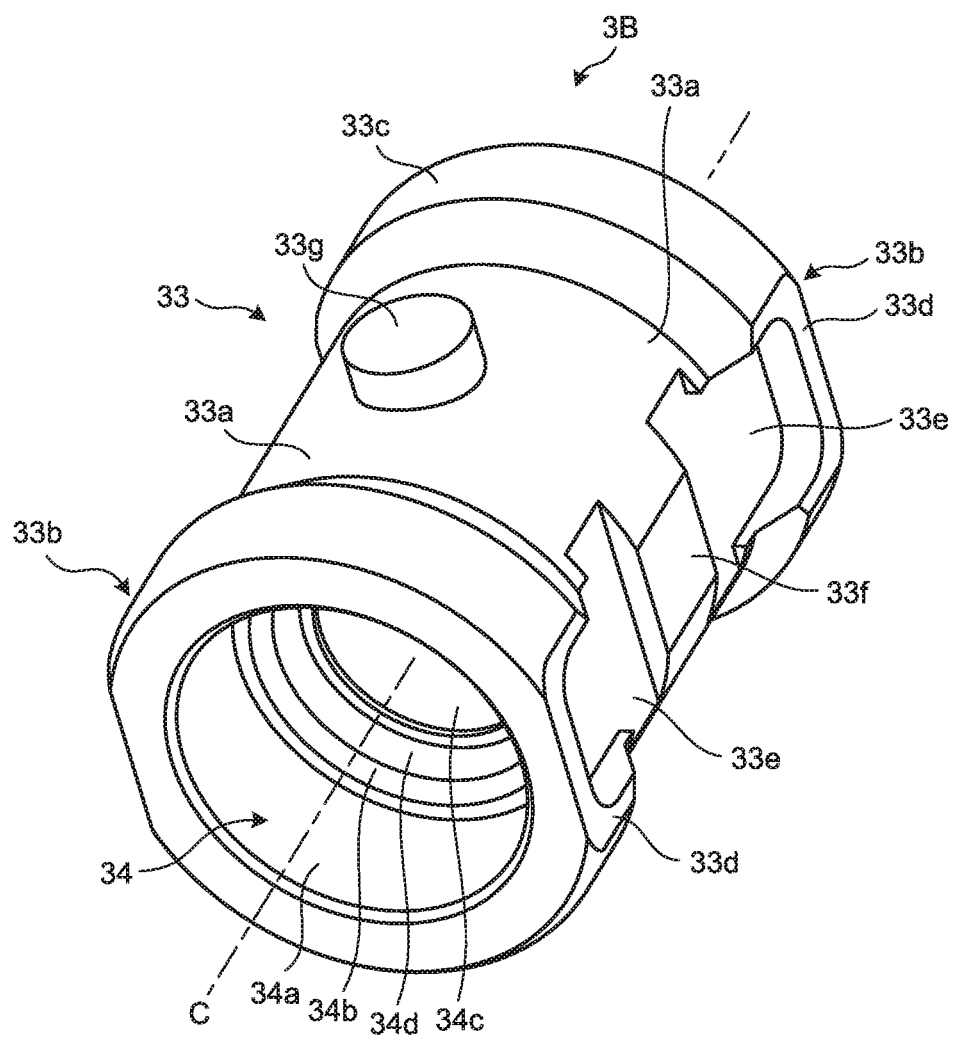
FIG. 19 is a perspective view illustrating a configuration of a movable member of the optical unit according to the third embodiment of the disclosure.

FIG. 19 is a perspective view illustrating a configuration of the movable member 3B. The movable member 3B illustrated in the figure is configured with a cylindrical member having an outer peripheral portion 33 and an inner peripheral portion 34.

The outer peripheral portion 33 has a cylinder 33*a* and two protruding edge portions 33*b* which are respectively formed on both end portions in the direction of the axis C of the cylinder 33*a* and are larger in outer diameter than that of the cylinder 33*a*. The cylinder 33*a* and the protruding edge portion 33*b* may be formed as an integral member or as separate members.

The protruding edge portion 33*b* has movable-side sliding surfaces 33*c* configured with an outer peripheral surface thereof and planar portions 33*d* formed on portions of the radial-direction outer side of the protruding edge portion 33*b*. In the case illustrated in FIG. 19, the protruding edge portion 33*b* alternately has two movable-side sliding surfaces 33*c* and two planar portions 33*d* along the peripheral direction around the axis C. The planar portions 33*d* pass through the same plane as any of the two planar portions 33*d* formed on the other end side along the direction of the axis C. In other words, the outer peripheral portion 33 has two sets of two planar portions 33*d* which are formed at different end portions and pass through the same plane.

Between the two sets of planar portions 33*d*, step difference portions 33*e* formed radially inward from the cylinder 33*a* and having a planar outer peripheral surface are provided, respectively. A cutout portion 33*f* having a planar outer periphery is provided at the central portion of the step difference portions 33*e* in the direction of the axis C by cutting out the surface of the cylinder 33*a*. A cylindrical rotation restricting member 33*g* which restricts rotation of the movable member 3B around the axis C is provided on the surface of the cylinder 33*a* which is in the middle in the peripheral direction perpendicular to the axis C of the cutout portion 33*f* so as to protrude from the surface of the cylinder 33*a*.

The inner peripheral portion 34 has a first inner peripheral portion 34*a*, a second inner peripheral portion 34*b*, a third inner peripheral portion 34*c*, and an inner peripheral side protrusion 34*d*. The second inner peripheral portion 34*b* is smaller in diameter than the first inner peripheral portion 34*a* and the third inner peripheral portion 34*c*. Between the second inner peripheral portion 34*b* and the third inner peripheral portion 34*c*, the inner peripheral side protrusion 34*d* protruding on the radial-direction inner side with the smallest diameter is provided. The second inner peripheral portion 34*b* retains the movable first lens Lv1 included in the movable lens group Gv. As illustrated in FIGS. 16 and 17, it is preferable that the image side of the movable first lens Lv1 is in contact with the inner peripheral side protrusion 34*d*.

The movable member 3B is inserted into the fixing member main body 20B while the movable-side sliding surface 33*c* is in contact with the fixed-side sliding surface 28. As illustrated in FIGS. 16 and 17, the movable member is inserted such that the first outer peripheral portion 51*a* of the rear frame portion 5 faces the radial-direction inner side of the third inner peripheral portion 34*c* of the movable member 3B. Thus, at least a portion of the image-side fixed lens group Gb is located on the radial-direction inner side of the third inner peripheral portion 34*c* of the movable member 3B. When the movable member 3B is moved to the most object side, at least a portion of the object-side fixed lens group Gf is located on the radial-direction inner side of the first inner peripheral portion 34*a* of the movable member 3B.

In the third embodiment, as illustrated in FIG. 15, the peripheral-direction width of the plane of the rotation restricting member 33*g* of the movable member 3B perpendicular to the axis C is smaller than the peripheral-direction width of the magnet 12 (the second magnet 12*b* is illustrated in FIG. 15) in the same plane. The rotation restricting member 33*g* is not provided between the first magnet 12*a* and the second magnet 12*b* along the direction of the axis C. For this reason, the rotation restricting member 33*g* has a columnar shape because there is no need for a space for arranging the first magnets 12*a* and the second magnets 12*b* on the object-side and the image side in the direction of the axis C, respectively. As a result, it is possible to facilitate machining of the rotation restricting member 33*g*.

The voice coil motor 10B has two sets in which the first magnet 12*a* and the second magnet 12*b* are arranged side by side along the axis C in this order. When viewed in the plane illustrated in FIG. 15, that is, the plane perpendicular to the axis C, two magnets (the second magnets 12*b* in FIG. 15) of the same type are provided every 180° along the peripheral direction.

According to the third embodiment of the disclosure described above, it is possible to obtain the same effects as those of the above-described first embodiment.

In addition, according to the third embodiment, the number of magnets 12 is reduced and the rotation restricting member 33*g* is also miniaturized, so that it is possible to further reduce the size and weight.

Fourth Embodiment

Figure 20:
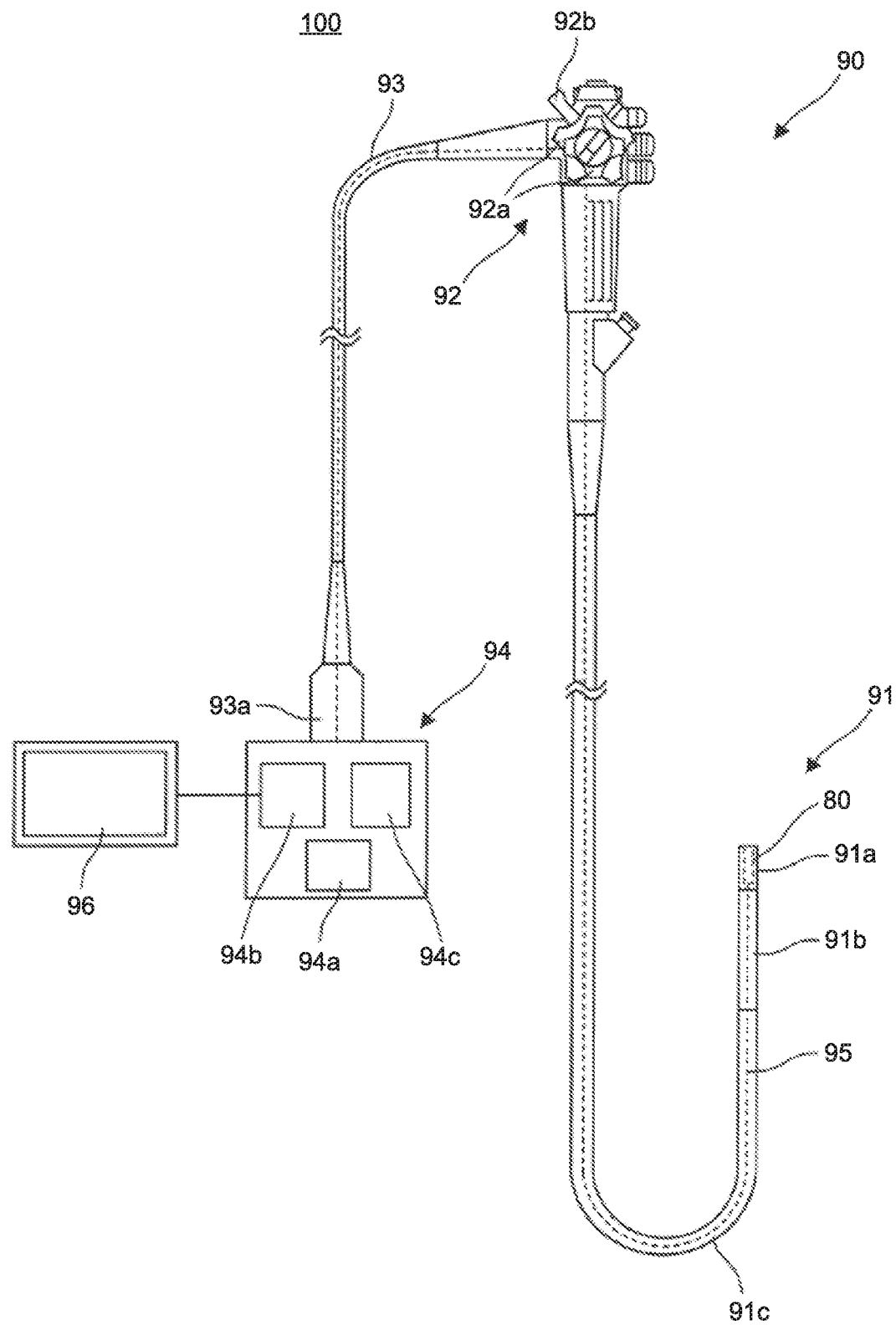
FIG. 20 is a view illustrating a configuration of an endoscope system including an endoscope according to a fourth embodiment of the disclosure.

FIG. 20 is a view illustrating a configuration of an endoscope system including an endoscope according to a fourth embodiment of the disclosure. An endoscope system 100 illustrated in the figure is configured to include an endoscope 90, a control device 94, and a display device 96. The endoscope 90 is configured to include any one of the optical units according to the first to third embodiments described above.

The endoscope 90 may be introduced into a subject such as a human body and optically captures a predetermined observed region inside the subject. In addition, the subject into which the endoscope 90 is introduced is not limited to a human body, but the subject may be another living body, or an artificial object such as a machine, a building, or the like. In other words, the endoscope 90 may be a medical endoscope or an industrial endoscope.

The endoscope 90 is configured to include an insertion unit 91 which is introduced into an inside of the subject, an operating unit 92 which is arranged at the proximal end of the insertion unit 91, and a universal cord 93 as a composite cable extending from the operating unit 92.

The insertion unit 91 is configured to include a distal end portion 91*a* arranged at the distal end, a bendable bending portion 91*b* arranged at the proximal end side of the distal end portion 91*a*, and a flexible tube portion 91*c* arranged on the proximal end side of the bending portion 91*b* and connected to the distal end side of the operating unit 92. An imaging unit 80 for collecting the light from the subject and capturing an image of the subject is provided at the distal end portion 91*a*. The imaging unit 80 is configured to include an optical unit 1, 1A, or 1B that collects light from the subject and an image sensor that photoelectrically converts the light collected by the optical unit 1, 1A, or 1B and outputs an electric signal. The image sensor is configured by using a charge coupled device (CCD) or complementary metal oxide semiconductor (CMOS). In addition, the endoscope 90 may be a rigid endoscope not having the flexible tube portion 91*c* in the insertion unit 91.

The operating unit 92 is configured to include an angle operating unit 92*a* for operating the bending state of the bending portion 91*b*, a zoom operating unit 92*b* for instructing the operation of the voice coil motor 10 described above and performing a zoom operation in the optical unit 1, 1A, or 1B. The angle operating unit 92*a* is formed in a knob shape, and the zoom operating unit 92*b* is formed in a lever shape. However, other forms such as a volume switch and a push switch may be used, respectively.

The universal cord 93 is a member for connecting the operating unit 92 and the control device 94. The endoscope 90 is connected to the control device 94 through a connector 93*a* provided to the proximal end portion of the universal cord 93.

Cables 95 such as wires, electric wires, and optical fibers are inserted through the insertion unit 91, the operating unit 92 and the universal cord 93.

The control device 94 is configured to include a driving control unit 94*a* which controls the bending state of the bending portion 91b, an image control unit 94b which controls the imaging unit 80, and a light source control unit 94c that controls a light source device (not illustrated). The control device 94 has a processor such as a central processing unit (CPU) and controls the entire endoscope system 100 in a centralized manner.

The driving control unit 94a has an actuator and is mechanically connected to the operating unit 92 and the bending portion 91b through a wire. The driving control unit 94a controls the bending state of the bending portion 91b by advancing and retreating the wire.

The image control unit 94b is electrically connected to the imaging unit 80 and the operating unit 92 through an electric wire. The image control unit 94b performs drive control of the voice coil motor 10 or 10B of the imaging unit 80 and processing of images captured by the imaging unit 80. The image processed by the image control unit 94b is displayed on the display device 96.

The light source control unit 94c is optically connected to the light source and the operating unit 92 through an optical fiber. The light source control unit 94c controls the brightness or the like of the light source emitted from the distal end portion 91a.

Alternatively, the operating unit 92 may be formed separately from the insertion unit 91, and the operation of the insertion unit 91 may be performed by remote operation.

Since the endoscope system 100 having the above configuration is configured to include the imaging unit 80 having the above-described optical unit 1, 1A, or 1B, it is possible to quickly change the zoom with a small size, and thus, the endoscope system is suitable for imaging moving picture.

In addition, according to the endoscope system 100, since the magnets 12 are provided to the movable member 3, 3A, or 3B and the coils 11 are provided to the fixing member 2 or 2B, there is no need to move the cable connected to the coils 11. For this reason, there is no possibility that the cable will move and cause disconnection in the limited space of the distal end portion of the endoscope 90, and the durability is also excellent.

Other Embodiments

Although the embodiments for carrying out the disclosure have been described heretofore, the disclosure should not be limited only by the embodiments described above. For example, it is possible to further include at least one magnetic detector for detecting a magnetic field with respect to the above-described optical unit 1, 1A, or 1B and a current control unit for controlling the current flowing in the coil 11 based on the detection result of the magnetic detector. The magnetic detector is realized by using, for example, a Hall element or a magnetoresistance effect element (MR element). The magnetic detector is fixedly provided to a support member provided on the radial-direction outer side of the coil 11. By controlling the current flowing in the coil 11 based on the magnetic field detected by the magnetic detector, it is possible to more accurately control the driving speed and stop position of the movable member 3, 3A, or 3B.

In addition, a plurality of rotation restricting members may be provided. In addition to realizing miniaturization and weight reduction, in order to provide an economical optical unit by suppressing the manufacturing cost without unnecessarily increasing the requirement accuracy for components, it is preferable that it is necessary to reduce the number of rotation restricting members as much as possible.

In addition, the number of magnets arranged in the movable member is not limited to those described in the first to third embodiments.

In addition, the recessed portion provided to the fixing member is only required to be able to assemble the rotation restricting member and the magnet, and the recessed portion may not penetrate to the radial-direction outer peripheral side.

According to the disclosure, it is possible to realize miniaturization and weight reduction of an actuator for moving a movable lens forward and backward.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:
1. An optical unit comprising:
a cylindrical fixing member configured to retain at least one of an object-side fixed lens group and an image-side fixed lens group;
a cylindrical movable member configured to retain a movable lens group between the object-side fixed lens group and the image-side fixed lens group and arranged on a radial-direction inner side of the fixing member so as to be slidable with respect to the fixing member, the cylindrical movable member having a same central axis as the cylindrical fixing member;
a voice coil motor including:
a coil arranged in the fixing member; and
magnets arranged on the movable member and magnetically polarized in a direction intersecting with the central axis;
the voice coil motor being capable of moving the movable member relative to the fixing member along a direction of the central axis; and
a rotation restricting member configured to restrict rotation of the movable member about the central axis with respect to the fixing member;
wherein the fixing member includes a recessed portion formed in at least a part of a cylindrical shape;
wherein the rotation restricting member is located in the recessed portion of the fixing member;
wherein the coil is wound around the central axis;
wherein the magnets are disposed symmetrically with respect to the central axis;
wherein the magnets includes a plurality of sets of a first magnet and a second magnet which are adjacent to each other along the direction of the central axis and of which magnetic polarization directions are opposite to each other in the radial-direction;
wherein a plurality of the first magnets have a same magnetic polarization direction;
wherein the coil includes:
a first coil facing the plurality of the first magnets; and
a second coil facing a plurality of the second magnets, the second coil being connected to the first coil; and
wherein the first coil and the second coil have opposite current flow directions.
2. The optical unit according to claim 1, wherein the rotation restricting member is arranged between at least one set of the first magnet and the second magnet adjacent to each other along the direction of the central axis.

3. The optical unit according to claim 1, wherein a width of the rotation restricting member in a peripheral direction perpendicular to the direction of the central axis is larger than a width of the magnet in the peripheral direction.

4. The optical unit according to claim 1, wherein at least a portion of the rotation restricting member being in contact with the fixing member has curved shape.

5. An endoscope which is inserted into an inside of a subject and observes the inside of the subject, the endoscope comprising:
   an optical unit comprising:
      a cylindrical fixing member configured to retain at least one of an object-side fixed lens group and an image-side fixed lens group;
      a cylindrical movable member configured to retain a movable lens group between the object-side fixed lens group and the image-side fixed lens group and arranged on a radial-direction inner side of the fixing member so as to be slidable with respect to the fixing member, the cylindrical movable member having a same central axis as the cylindrical fixing member;
      a voice coil motor including:
         a coil arranged in the fixing member; and
         magnets arranged on the movable member and magnetically polarized in a direction intersecting with the central axis,
         the voice coil motor being capable of moving the movable member relative to the fixing member along a direction of the central axis; and
      a rotation restricting member configured to restrict rotation of the movable member about the central axis with respect to the fixing member;
      wherein the fixing member includes a recessed portion formed in at least a part of a cylindrical shape;
      wherein the rotation restricting member is located in the recessed portion of the fixing member;
      wherein the coil is wound around the central axis;
      wherein the magnets are disposed symmetrically with respect to the central axis;
      wherein the magnets includes a plurality of sets of a first magnet and a second magnet which are adjacent to each other along the direction of the central axis and of which magnetic polarization directions are opposite to each other in the radial-direction;
      wherein a plurality of the first magnets have a same magnetic polarization direction;
      wherein the coil includes:
         a first coil facing the plurality of the first magnets; and
         a second coil facing a plurality of the second magnets; the second coil being connected to the first coil; and
      wherein the first coil and the second coil have opposite current flow directions; and
   an image sensor configured to convert light condensed by the optical unit into an electrical signal.

* * * * *